United States Patent
Bondinell et al.

(10) Patent No.: US 6,242,459 B1
(45) Date of Patent: Jun. 5, 2001

(54) SUBSTITUTED BIS-ACRIDINES AND RELATED COMPOUNDS AS CCR5 RECEPTOR LIGANDS, ANTI-INFLAMMATORY AGENTS AND ANTI-VIRAL AGENTS

(75) Inventors: William E. Bondinell, Wayne, PA (US); Valerie A. Reader, Princeton, NJ (US); Thomas Wen Fu Ku, Dresher, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/341,171

(22) PCT Filed: Jan. 8, 1998

(86) PCT No.: PCT/US98/00489

§ 371 Date: Jul. 2, 1999

§ 102(e) Date: Jul. 2, 1999

(87) PCT Pub. No.: WO98/30298

PCT Pub. Date: Jul. 16, 1998

Related U.S. Application Data

(60) Provisional application No. 60/035,148, filed on Jan. 8, 1997.

(51) Int. Cl.[7] ............... A61K 31/473; C07D 219/12; A61P 29/00
(52) U.S. Cl. ............... 514/297; 546/103; 546/106
(58) Field of Search .................. 546/103, 106; 514/297

(56) References Cited

U.S. PATENT DOCUMENTS

| | | | |
|---|---|---|---|
| 2,503,899 | 4/1950 | Britton et al. | 260/279 |
| 5,328,916 | * 7/1994 | Raddatz | 514/318 |
| 5,534,654 | * 7/1996 | Ohtani | 564/90 |
| 5,614,531 | * 3/1997 | Juraszyk | 514/300 |

FOREIGN PATENT DOCUMENTS

| | | |
|---|---|---|
| 2 314 165 | 1/1977 | (FR) . |
| 2 588 259 | 4/1987 | (FR) . |
| 62-281830 | 12/1987 | (JP) . |
| 4 226 467 | 8/1992 | (JP) . |

OTHER PUBLICATIONS

Fico RM et al. Science. 198, pp. 53–55, Oct. 1977.*
Taylor JL et al. Mol. Pharmacol. 45(1), pp. 74–83, 1994.*
Raport CJ et al. J. Biol. Chem. 27(29), pp. 17161–17166, Jul. 1996.*
Derwent Publication Ltd., London, GB, AN 1992–320813, XP002135200, (1992).
Derwent Publication Ltd., London, GB, AN 1988–018794, XP002135201, (1988).
Bender et al., "Poly (anthrylenetrimethylene) and 9,10–Bridged Anthracenes by Reductive Alkylation", Angewandte Chemie. International Edition., XP002135199, (1986).
Chem. abstract., vol. 78, No. 11, Mar. 19, 1973, p. 451, column 1, abstract no. 71877n, Stefanska, B., "Research on Tumor Inhibiting Compounds. LI.1–Nitro–9–Aminoacridine and 1–Nitro–N10–Methyl–9–Amino–Acridium–N9–Derivatives".
J. Med. Chem. 1978, vol. 21, No. 9, pp. 868–874, Chen et al. Diacridines, bifunctional intercalators, Chemistry and antitumor activity.

* cited by examiner

*Primary Examiner*—Evelyn Mei Huang
(74) *Attorney, Agent, or Firm*—Nora Stein-Fernandez; Stephen Venetianer; Charles M. Kinzig

(57) ABSTRACT

This invention relates to substituted bis-acridines and related compounds which are ligands, in particular, antagonists of the CCR5 receptor. In addition, this invention relates to the treatment and prevention of disease states mediated by CCR5, including, but not limited to, asthma and atopic disorders, rheumatoid arthritis, atherosclerosis, psoriasis, auto immune diseases such as multiple sclerosis, and inflammatory bowel disease, all in mammals, by the use of substituted bis-acridines and related compounds which are CCR5 receptor antagonists. Also, since CCR5 is a co-receptor for the entry of HIV into cells, selective receptor ligands may be useful in the treatment of HIV infection.

3 Claims, No Drawings

SUBSTITUTED BIS-ACRIDINES AND RELATED COMPOUNDS AS CCR5 RECEPTOR LIGANDS, ANTI-INFLAMMATORY AGENTS AND ANTI-VIRAL AGENTS

This application is the national phase of PCT/US98/00489, filed Jan. 8, 1998 which claims the benefit of provisional application 60/035,148, filed Jan. 8, 1997.

FIELD OF THE INVENTION

This invention relates to substituted bis-acridines and related compounds which are ligands, agonists or antagonists, of the CC chemokine receptor CC-CKR5 now designated as CCR5 (*Nature Medicine* 1996, 2, 1174–8). In addition, this invention relates to the treatment and prevention of disease states mediated by CCR5.

BACKGROUND OF THE INVENTION

T cells are not only key regulators of the immune response to infectious agents but are believed critical for the initiation and maintenance of the inflammatory reaction in a variety of chronic diseases. Increased numbers or enhanced activation state of T cells, especially CD4+ T cells, have been demonstrated in the synovium of individuals with rheumatoid arthritis (M. J. Elliott and R. N. Maini, *Int. Arch. Allergy Immunol.* 104: 112–1125, 1994), in the bronchial mucosa of asthmatics (C. J. Corrigan and A. B. Kay, *Immunol. Today* 13: 501–506, 1992), in the lesions of multiple sclerosis (R. Martin and H. F. McFarland, *Crit. Rev. Clin. Lab. Sci.* 32: 121–182, 1995), in psoriatic lesions (J. L. Jones, J. Berth-Jone, A. Fletcher and P. E. Hutchinson, *J. Pathol.* 174: 77–82, 1994) and in the fatty streaks of atherosclerosis (R. Ross, *Annu. Rev. Physiol.* 57: 791–804, 1995).

T cells, as well as other inflammatory cells, will migrate into tissues in response to the production of a variety chemotactic factors. Among these factors are a superfamily of 8–12 kDa proteins known as the chemokines. These proteins share structural features such as the presence of 3–4 conserved cysteine residues. RANTES, which stands for Regulated upon Activation Normal T cell Expressed and Secreted, is a 8 kDa protein member of CC branch of the chemokine family. These proteins recruit and activate immune and inflammatory cells through an interaction with G-protein coupled receptors. The CC branch is defined by the absence of an intervening amino acid residue between the first two cysteine residues and members of this family predominately elicit the migration of mononuclear cells, eosinophils and basophils (M. Baggiolini, B. Dewald, and B. Moser, *Adv. Immunol.* 55:97–179, 1994; and J. J. Oppenheim, C. O. C. Zachariae, N. Mukaida, and K. Matsushima, *Annu. Rev. Immunol.* 9: 617–648, 1991).

RANTES potently produces chemotaxis of T cells, basophils, eosinophils, monocytes and mast cells. RANTES was originally identified as gene product induced late after antigen activation of T-cells (T. J. Schall, J. Jongstra, B. J. Dyer, J. Jorgensen, et al., *J. Immunol.* 141:1018–1025, 1988), however, RANTES has been shown to be synthesized and secreted by a diverse group of cells that include epithelial and endothelial cells (C. Stellato, L. A. Beck, G. A. Gorgone, D. Proud, et al., *J. Immunol.* 155: 410–418, 1995; and A. Marfaing-Koka, O. Devergne, G. Gorgone, A. Portier, et al., *J. Immunol.* 154: 1870–1878, 1994), synovial fibroblasts (P. Rathanaswami, M. Hachicha, M. Sadick, T. J. Schall, et al., *J. Biol. Chem.* 268: 5834–5839, 1993) and dermal fibroblasts (M. Sticherling, M. Kupper, F. Koltrowitz, E. Bornscheuer, et al., *J. Invest. Dermatol.* 105: 585–591, 1995), mesangial cells (G. Wolf, S. Aberle, F. Thaiss, et al., *Kidney Int.* 44: 795–804, 1994) and platelets (Y. Koameyoshi, A. Dorschner, A. I. Mallet, E. Christophers, et al., *J. Exp. Med.* 176: 587–592, 1992). In these cells RANTES mRNA is rapidly upregulated in response to IL-1 or TNFa. Although RANTES mRNA is not usually detected in normal tissues (J. M. Pattison, P. J. Nelson, and A. M. Krensky, *Clin. Immunother.* 4: 1–8, 1995), increased mRNA or protein has been found in diseases characterized by a mononuclear infiltrate. For example, RANTES mRNA was visualized using in situ hybridization in renal allografts undergoing rejection (J. M. Pattison, P. J. Nelson, and A. M. Krensky, *Clin. Immunother.* 4: 1–8, 1995; and K. C. Nadeau, H. Azuma and N. I. Tilney, *Proc. Natl. Acad. USA* 92: 8729–8733, 1995) in the skin of atopic dermatitis patients after exposure to antigen (S. Ying, L. Taborda-Barata, Q. Meng, M. Humbert, et al., *J. Exp. Med.* 181: 2153–2159, 1995), and in endothelial cells of coronary arteries undergoing accelerated atherosclerosis after cardiac transplant (J. M. Pattison, P. J. Nelson, and A. M. Krensky, *Clin. Immunother.* 4: 1–8, 1995). Further, increased immunoreactive protein for RANTES has been detected in bronchoalveolar lavage fluid (R. Alam, J. York, M. Boyers, et al., *Am. J. Resp. Crit. Care Med.* 149: A951, 1994) and sputum from asthmatic individuals (C. M. Gelder, P. S. Thomas, D. H. Yates, I. M. Adcock, et al., *Thorax* 50: 1033–1037, 1995).

Several receptors have been identified that bind RANTES. In particular, CCR5, when expressed in either HEK 293 cells or CHO cells, binds RANTES. This receptor is expressed in T-cells and in monocytes and macrophages, immune/inflammatory cells which are important in the maintenance of a chronic inflammatory reaction. Pharmacological characterization of CCR5 indicates similarities to the RANTES binding site observed on isolated T cells. Therefore, antagonism of RANTES' action on CCR5, as well as antagonism of other natural ligands of CCR5, should inhibit the recruitment of T cells into inflammatory lesions and provide a novel therapeutic approach for the treatment of atopic and autoimmune disorders.

Since T cells express CCR5, selective receptor ligands of CCR5, particularly antagonists, are likely to provide beneficial effects in diseases including, but not limited to, asthma and atopic disorders (for example, atopic dermatitis and allergies), rheumatoid arthritis, atherosclerosis, psoriasis, autoimmune diseases such as multiple sclerosis, and inflammatory bowel disease, all in mammals, preferably humans. Also since CCR5 is a co-receptor for the entry of HIV into cells, selective receptor ligands may be useful in the treatment of HIV infection.

A subset of compounds included in formula (I) have been reported to have intercalating activity (*J. Med. Chem.* 1978, 21, 868–74; *Biochem. Pharmacol.* 1977, 26, 275–8; and *J. Med. Chem.* 1978, 21, 658–68), mutagenic activity (*Mutat. Res.* 1990, 232, 337–43; and *Biochem. J.* 1985, 226, 175–82), antitumor activity (*Biochem. Pharmacol.* 1985, 34, 2123–8), antibacterial, antitubercular, and antileprotic activity (*Chem. Pharm. Bull.* 1972, 20, 206–8), and anti-acetylcholinesterase activity (*Anal. Spectrosc. Libr.* 1995, 6, 281–311).

Surprisingly, it has now been discovered that this class of non-peptide compounds, in particular substituted bis-acridines and related compounds of formula (I), function as CCR5 receptor ligands, agonists or antagonists, and therefore, have utility in the treatment of disease states wherein inhibition of CCR5 receptor mechanisms is indicated for prevention or therapeutic treatment.

SUMMARY OF THE INVENTION

In one aspect, the present invention is to a method of treating CCR5 mediated disease states, including, but not limited to, asthma and atopic disorders (for example, atopic dermatitis and allergies), rheumatoid arthritis, atherosclerosis, psoriasis, autoimmune diseases such as multiple sclerosis, inflammatory bowel disease, and HIV infection, all in mammals, preferably humans, comprising administering to such mammal in need thereof, an effective amount of a substituted bis-acridine or related compound of formula (I), or pharmaceutically active salts thereof:

Formula (I)

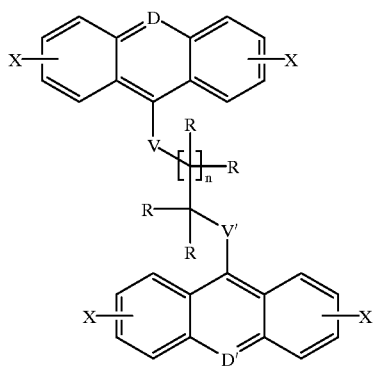

wherein:

X are independently one or more of H, optionally substituted $C_{1-6}$alkyl, $C_{3-7}$cycloalkyl-$C_{0-4}$alkyl, Ar-$C_{0-4}$alkyl, $CH_2NR'_2$, $CH_2OR'$, CN, COR', $CONR'_2$, $CO_2R'$, $CF_3$, $N(R')_2$, NR'COR', NR'CONR'R', $NR'CO_2R''$, $NR'SO_2R''$, $NO_2$, OR', $S(O)_{0-2}R''$, $S(O)_{0-2}CF_3$, or halo;

R' is H, optionally substituted $C_{1-6}$alkyl, $C_{3-7}$cycloalkyl-$C_{0-4}$alkyl or Ar-$C_{0-4}$alkyl;

R" is $C_{1-6}$alkyl, $C_{3-7}$cycloalkyl-$C_{0-4}$alkyl or Ar-$C_{0-4}$alkyl;

D and D' are independently CX or N;

V and V' are independently $C(R)_2$, $NR_1$, O, or $S(O)_{0-2}$;

$R_1$ are independently H, $C_{1-6}$alkyl, $C_{3-7}$cycloalkyl-$C_{0-4}$alkyl,

Ar-$C_{0-4}$alkyl, —$C(O)CF_3$, —C(O)R', or —$SO_2R''$, or, when V and V' are —$NR_1$, the two $R_1$ groups taken together may be $(C(R)_2)_{2-3}$ to form a heterocyclic ring of five to nine members;

n is 0, 1, 2 or 3; and

R are independently H, $C_{1-6}$alkyl, $C_{3-7}$cycloalkyl-$C_{0-4}$alkyl or Ar-$C_{0-4}$alkyl, or, when V and V' are independently $NR^1$, O or $S(O)_{0-2}$, any two R taken together may be $(C(R)_2)_{2-4}$ to form a carbocyclic ring of three to eight members.

In another aspect, the present invention is to a genus of novel compounds of formula (I), or pharmaceutically active salts thereof, said compounds which are also useful in treating the above-mentioned CCR5-mediated disease states:

Formula (I)

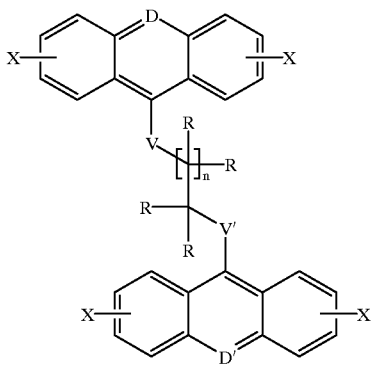

wherein:

X are independently one or more of H, optionally substituted $C_{1-6}$alkyl, $C_{3-7}$cycloalkyl-$C_{0-4}$alkyl, Ar-$C_{0-4}$alkyl, $CH_2NR'_2$, $CH_2OR'$, CN, COR', $CONR'_2$, $CO_2R'$, $CF_3$, $N(R')_2$, NR'COR', NR'CONR'R', $NR'CO_2R''$, $NR'SO_2R''$, $NO_2$, OR', $S(O)_{0-2}R''$, $S(O)_{0-2}CF_3$, or halo;

R' is H, optionally substituted $C_{1-6}$alkyl, $C_{3-7}$cycloalkyl-$C_{0-4}$alkyl or Ar-$C_{0-4}$alkyl;

R" is $C_{1-6}$alkyl, $C_{3-7}$cycloalkyl-$C_{0-4}$alkyl or Ar-$C_{0-4}$alkyl;

D and D' are independently CX or N;

V and V' are independently $C(R)_2$, $NR_1$, O, or $S(O)_{0-2}$;

$R_1$ are independently H, $C_{1-6}$alkyl, $C_{3-7}$cycloalkyl-$C_{0-4}$alkyl, Ar-$C_{0-4}$alkyl, —$C(O)CF_3$, —C(O)R', or —$SO_2R''$, or, when V and V' are —$NR_1$, the two $R_1$ groups taken together may be $(C(R)_2)_{2-3}$ to form a heterocyclic ring of five to nine members;

n is 0, 1, 2 or 3; and

R are independently H, $C_{1-6}$alkyl, $C_{3-7}$cycloalkyl-$C_{0-4}$alkyl or Ar-$C_{0-4}$alkyl, or, when V and V' are independently $NR^1$, O or $S(O)_{0-2}$, any two R taken together may be $(C(R)_2)_{2-4}$ to form a carbocyclic ring of three to eight members, with the proviso that the compound of formula (I) is not 9,9'-(1,3-propanediyl)bis-acridine; 9,9'-(1,5-pentanediyl)bis-acridine; N,N'-di-9-acridinyl-1,2ethanediamine; N,N'-bis(4-ethyl-9-acridinyl)-1,2-ethanediamine; N,N'-bis(3-methoxy-9-acridinyl)-1,2-ethanediamine; N,N'-bis(4butoxy-9-acridinyl)-1,2-ethanediamine; N,N'-bis(6-chloro-2-methoxy-9-acridinyl)-1,2-ethanediamine; trans-N,N'-bis(6chloro-2-methoxy-9-acridinyl)-1,2-cyclohexanediamine; 9,9'-(1,4-piperazinediyl)bis[6-chloro-2-methoxy-acridine]; N,N'-di-9-acridinyl-1,2-propanediamine; N,N'-di-9-acridinyl-1,3-propanediamine; N,N'-bis(1-nitro-9-acridinyl)-1,3-propanediamine; N,N'-bis(6chloro-2-methoxy-9-acridinyl)-1,3-propanediamine; N,N'-bis(6-chloro-2-methoxy-9-acridinyl)-2,2-methyl-1,3-propanediamine; N,N'-bis(6chloro-2-fluoro-9-acridinyl)-1,3-propanediamine; N,N'-di-9-acridinyl-1,4-butanediamine; N,N'-bis(4-ethyl-9-acridinyl)-1,4-butanediamine; N,N'-bis(1-nitro-9-acridinyl)-1,4-butanediamine; N,N'-bis(3-methoxy-9-acridinyl)-1,4-butanediamine; N,N'-bis(4-propoxy-9-acridinyl)-1,4-butanediamine; N,N'-bis(6chloro-2-methoxy-9-acridinyl)-1,4-butanediamine; N,N'-bis(3,6-dichloro-9-acridinyl)-1,4-butanediamine; 6-chloro-N-[2-[(6-chloro-2-methoxy-9-acridinyl)thio]ethyl]-2-methoxy-9-acridinamine; 9,9'-[1,2-ethanediylbis(thio)]bis-acridine; 9,9'-[1,2-ethanediylbis(thio)]bis-3- acridinamine; 9,9'-[1,3-propanediylbis(thio)]bis-acridine; 9,9-[1,4-butanediylbis(thio)]bis-acridine; 9,9'-[1,4-butanediylbis(thio)]bis-3-acridinamine; 9,9'-[1,4-butanediylbis(thio)]bis-4-acridinamine; 9,9'-[1,4-butanediylbis(thio)]bis4-acridinamine; 9,9'-[methylenebis(oxy)]bis-anthracene; 9,9'-[methylenebis(oxy)]bis[10-methoxy-anthracene]; 9,9'-[methylenebis(oxy)]bis [10-propoxy-anthracene]; 9,9'-[methylenebis(oxy)]bis[10-(2-methoxyethoxy)-anthracene]; 9,9'-[1,2-ethanediylbis(oxy)]bis-anthracene; 9,9'-(1,3-propanediyl)bis-anthracene; 9,9'-(1,4-butanediyl)bis-anthracene; 9,9'-(1,4-butanediyl)bis[10-(chloromethyl)-anthracene; 9-[3-(9-anthracenyloxy)propyl]anthracene; 9,9'-(1,5-pentanediyl)bis-anthracene; 9,9'-(1,5-pentanediyl)bis[10-(chloromethyl)-anthracene; and 9,9'-(1,6-hexanediyl)bis-anthracene.

In yet another aspect, the present invention is to pharmaceutical compositions comprising a compound of formula (I) and a pharmaceutically acceptable carrier therefor. In particular, the pharmaceutical compositions of the present invention are used for treating CCR5-mediated disease states, including, but not limited to, asthma and atopic disorders (for example, atopic dermatitis and allergies), rheumatoid arthritis, atherosclerosis, psoriasis, autoimmune diseases such as multiple sclerosis, inflammatory bowel disease, and HIV infection.

DETAILED DESCRIPTION OF THE INVENTION

It has now been discovered that substituted bis-acridines and related compounds of formula (I) are CCR5 receptor ligands. It has also now been discovered that selective inhibition of CCR5 receptor mechanisms by treatment with the receptor ligands of formula (I), or a pharmaceutically acceptable salt thereof, represents a novel therapeutic and preventative approach to the treatment of a variety of disease states, including, but not limited to, asthma and atopic disorders (for example, atopic dermatitis and allergies), rheumatoid arthritis, atherosclerosis, psoriasis, autoimmune diseases such as multiple sclerosis, inflammatory bowel disease, and HIV infection, all in mammals, preferably humans.

The term "alkyl" is used herein at all occurrences to mean a straight or branched chain radical of 1 to 6 carbon atoms, unless the chain length is limited thereto, including, but not limited to methyl, ethyl, n-propyl, isopropyl, n-butyl, sec-butyl, isobutyl, tert-butyl, and the like.

The term "cycloalkyl" is used herein at all occurrences to mean cyclic radicals, preferably of 3 to 7 carbons, including but not limited to cyclopropyl, cyclopentyl, cyclohexyl, and the like.

The terms "halo" or "halogen" are used interchangeably herein at all occurrences to mean radicals derived from the elements chlorine, fluorine, iodine and bromine.

The terms "heteroring" or "heterocyclic ring" is used herein at all occurrences to mean a saturated or wholly or partially unsaturated 5-, 6-, 7-, 8- or 9-membered ring system which contains one or more heteroatoms selected from the group consisting of N, O, or S; such as, but not limited to, pyrrolidine, piperidine, piperazine, morpholine, imidazolidine or pyrazolidine.

The terms "aryl" or "Ar—" are used herein at all occurrences to mean substituted and unsubstituted aromatic ring(s) or ring systems which may include bi- or tri-cyclic systems. Representative examples include, but are not limited to, phenyl, benzyl, and naphthyl.

The term "optionally substituted" is used herein at all occurrences to mean that the moiety may or may not be substituted with one or more functional groups including —$OCH_3$, —$N(R')_2$ and —$CO_2R''$. It will be understood that the optional substituents are selected independently from one another.

It will be understood that the substituent(s) X may be at any open position on the aromatic rings of formula (I) to which the substituent is attached. In addition, it will be understood that there may be more than one substituent X in any given compound of formula (I), and that if there is more than one substituent X, that substituent may be the same or different.

The term "CCR5 mediated disease state" is used herein at all occurrences to mean any disease state which is mediated (or modulated) by CCR5.

Suitably, pharmaceutically acceptable salts of formula (I) include, but are not limited to, salts with inorganic acids such as hydrochloride, sulfate, phosphate, diphosphate, hydrobromide, and nitrate, or salts with an organic acid such as malate, maleate, fumarate, tartrate, succinate, citrate, acetate, lactate, methanesulfonate, p-toluenesulfonate, palmitate, salicylate, and stearate. In addition, pharmaceutically acceptable salts of compounds of formula (I) may also be formed with a pharmaceutically acceptable cation, for instance, if a substituent group comprises a carboxy moiety. Suitable pharmaceutically acceptable cations are well known to those skilled in the art and include alkaline, alkaline earth, ammonium and quaternary ammonium cations.

For the compounds of formula (I) various embodiments are as follows.

X is suitably independently one or more of H, optionally substituted $C_{1-6}$alkyl, $C_{3-7}$cycloalkyl-$C_{0-4}$alkyl, Ar-$C_{0-4}$alkyl, $CH_2NR'_2$, $CH_2OR'$, CN, COR', $CONR'_2$, $CO_2R'$, $CF_3$, $NR'_2$, NR'COR', NR'CONR'R', $NR'CO_2R''$, $NR'SO_2R''$, $NO_2$, OR', $S(O)_{0-2}R''$, $S(O)_{0-2}CF_3$, or halo. X is preferably 2-OR' and 6-Cl.

R' is suitably H, optionally substituted $C_{1-6}$alkyl, $C_{3-7}$cycloalkyl-$C_{0-4}$alkyl or Ar-$C_{0-4}$alkyl. R' is preferably H or optionally substituted $C_{1-6}$alkyl, more preferably $CH_3$, neopentyl, or t-butoxycarbonylmethyl.

R" is suitably $C_{1-6}$alkyl, $C_{3-7}$cycloalkyl-$C_{0-4}$alkyl or Ar-$C_{0-4}$alkyl. R" is preferably $C_{1-6}$alkyl.

D and D' are suitably independently CX or N. D and D' are preferably N.

V and V' are suitably independently $C(R)_2$, $NR^1$, O, or $S(O)_{0-2}$. V and V' are preferably $NR^1$.

$R^1$ are suitably independently H or $C_{1-6}$alkyl, $C_{3-7}$cycloalkyl-$C_{0-4}$alkyl, Ar-$C_{0-4}$alkyl, —$C(O)CF_3$, —C(O)R', —$SO_2R''$, or, when V and V' are —$NR^1$, the two $R^1$ groups taken together may be $(C(R)_2)_{2-3}$ to form a heterocyclic ring of five to nine members. $R^1$ is preferably H or one of $R^1$ is —$CO(CF_3)$.

Variable n is suitably 0, 1, 2 or 3. It will be understood that when V is $NR^1$ and V' is NR$^1$, O or S, n can be 0, 1, 2, or 3, except that this invention does not include compounds that are understood to be unstable when n is 0. Variable n is preferably 1.

R are suitably independently H, $C_{1-6}$alkyl, $C_{3-7}$cycloalkyl-$C_{0-4}$alkyl or Ar-$C_{0-4}$alkyl, or, when V and V' are independently $NR^1$, O or $S(O)_{0-2}$, any two R taken together may be $(C(R)_2)_{2-4}$ to form a carbocyclic ring of three to eight members. R is preferably H.

Among the preferred compounds of the invention are the following compounds:

N,N'-bis(6-chloro-2-methoxy-9-acridinyl)-1,2-ethanediamine bis(trifluoroactate);

N,N'di-9-acridinyl-1,2-ethanediamine bis(trifluoroactate);

N,N'-bis(6-chloro-2-methoxy-9-acridinyl)-1,3-propanediamine bis(trifluoroactate);

9,9'-(1,4-piperazinediyl)bis[6-chloro-2-methoxy-acridine]bis(trifluoroacetate);

N-(6-chloro-2-methoxy-9-acridinyl)-N'-(6-chloro-2-hydroxy-9-acridinyl)-1,2-ethanediamine bis(trifluoroacetate);

N,N'-bis(6-chloro-2-hydroxy-9-acridinyl)-1,2-ethanediamine bis(trifluoroactate);

N-[6-chloro-2-(2,2-dimethylpropoxy)-9-acridinyl]-N'-(6-chloro-2-hydroxy-9-acridinyl]-1,2-ethanediamine bis(trifluoroactate);

N-[6-chloro-2-(2,2-dimethylpropoxy)-9-acridinyl)-N'-(6-chloro-2-methoxy-9-acridinyl]-1,2-ethanediamine bis(trifluoroactate);

N,N'-bis(6-chloro-2-(2,2-dimethylpropoxy)-9-acridinyl]-1,2-ethanediamine bis(trifluoroactate);

N,N'-Bis[6-chloro-2-(tert-butoxycarbonyl)methoxy-9-acridinyl]-1,2-ethanediamine bis(trifluoroactate);

N-[6-chloro-2-(tert-butoxycarbonyl)methoxy-9-acridinyl]-N'-(6-chloro-2-hydroxy-9-acridinyl)-1,2-ethanediamine bis(trifluoroactate);

N-[6-chloro-2-(tert-butoxycarbonyl)methoxy-9-acridinyl]-N'-(6-chloro-2-methoxy-9-acridinyl)-1,2-ethanediamine bis(trifluoroactate);

N,N'-bis[(6-chloro-2-carboxymethoxy-9-acridinyl)-1,2-ethanediamine bis(trifluoroactate);

N-[6-chloro-2-(2-dimethylamino)ethoxy-9-acridinyl)-N'-(6-chloro-2-hydroxy-9-acridinyl]-1,2-ethanediamine bis(trifluoroactate);

N,N'-bis(6-chloro-2-methoxy-9-acridinyl)-N,N'-dimethyl-1,2-ethanediamine bis(trifluoroactate);

N,N'-bis(6-chloro-2-methoxy-9-acridinyl)-N,N'-bis(trifluoromethylcarbonyl)-1,2-ethanediamine bis(trifluoroactate);

N,N'-bis(6chloro2-methoxy-9-acridinyl)-N-(trifluoromethylcarbonyl)-1,2-ethanediamine bis(trifluoroacetate);

Bis(6-chloro-2-methoxy-9-acridinyl)-1,3-propane;

Bis(2-methoxy-9-acridinyl)-1,4-butane bis(trifluoroactate);

1-(6-chloro-2-methoxy-9-acridinyl)-4-(2-methoxy-9-acridinyl)butane;

N-(9-acridinyl)-N'-(6-chloro2-methoxy-9-acridinyl)-1,2-ethanediamine bis(trifluoroactate); and N,N'-bis(6chloro-2-methoxy-9-acridinyl)-N,N'-bis(acetyl)-1,2-ethanediamine.

A preferred group of compounds falling within the scope of formula (I) are compounds of formula (IA) or pharmaceutically acceptable salts thereof:

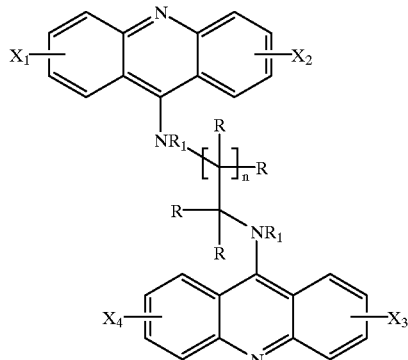

Formula (IA)

wherein:
$X_1$, $X_2$, $X_3$ and $X_4$ are independently H, optionally substituted $C_{1-6}$alkyl, $C_{3-7}$cycloalkyl-$C_{0-4}$alkyl, Ar-$C_{0-4}$alkyl, $CH_2NR'_2$, $CH_2OR'$, CN, $COR'$, $CONR'_2$, $CO_2R'$, $CF_3$, $N(R')_2$, $NR'COR'$, $NR'CONR'R'$, $NR'CO_2R''$, $NR'SO_2R''$, $NO_2$, $OR'$, $S(O)_{0-2}R''$, $S(O)_{0-2}CF_3$, or halo;

R' is H, optionally substituted $C_{1-6}$alkyl, $C_{3-7}$cycloalkyl-$C_{0-4}$alkyl or Ar-$C_{0-4}$alkyl;

R" is $C_{1-6}$alkyl, $C_{3-7}$cycloalkyl-$C_{0-4}$alkyl or Ar-$C_{0-4}$alkyl;

$R_1$ are independently H, $C_{1-6}$alkyl, $C_{3-7}$cycloalkyl-$C_{0-4}$alkyl, Ar-$C_{0-4}$alkyl, —$C(O)CF_3$, —$C(O)R'$, or —$SO_2R''$, or, the two $R_1$ groups taken together may be $(C(R)_2)_{2-3}$ to form a heterocyclic ring of five to nine members;

n is 0, 1, 2 or 3; and

R are independently H, $C_{1-6}$alkyl, $C_{3-7}$cycloalkyl-$C_{0-4}$alkyl or Ar-$C_{0-4}$alkyl, or, any two R taken together may be $(C(R)_2)_{2-4}$ to form a carbocyclic ring of three to eight members, provided that when n is 1, 2 or 3, $R_1$ are both H, and R are all H, $X_1$, $X_2$, $X_3$ and $X_4$ are not all hydrogen; and, provided that when n is 1, $R_1$ are both H, and one of R is $CH_3$, $X_1$, $X_2$, $X_3$ and $X_4$ are not all hydrogen; and, provided that when n is 1, $R_1$ are both H, R are all H, and $X_2$ and $X_3$ are each hydrogen, $X_1$ and $X_4$ are not each 4-ethyl, 3-methoxy or 4-butoxy; and, provided that when n is 1, and $R_1$ are both H, $X_1$, $X_2$, $X_3$ and $X_4$ are not 2-methoxy-6-chloro; and, provided that when the two $R_1$ groups taken together are $(CH_2)_2$ and form a 6-membered heterocyclic ring, and R are all H, $X_1$, $X_2$, $X_3$ and $X_4$ are not 2-methoxy-6-chloro; and, provided that when n is 1, $R_1$ are both H, two R are $(CH_2)_4$ to form a six-membered carbocyclic ring, and all other R are H, $X_1$, $X_2$, $X_3$ and $X_4$ are not 2-methoxy-6-chloro; and, provided that when n is 2, $R_1$ are both H, $R_1$ are all H, and $X_2$ and $X_3$ are each hydrogen, $X_1$ and $X_4$ are not each 1-$NO_2$; and, provided that when n is 2, $R_1$ are both H, and R are all H, $X_1$, $X_2$, $X_3$ and $X_4$ are not 2-methoxy-6-chloro or 2-fluoro-6-chloro; and, provided that when $[C(R)_2]_nC(R)_2$ is $CH_2C(CH_3)_2CH_2$, $X_1$, $X_2$, $X_3$ and $X_4$ are not 2-methoxy-6-chloro; and, provided that when n is 3, $R_1$ are both H, R are all H, and $X_2$ and $X_3$ are each hydrogen, $X_1$ and $X_4$ are not each 4ethyl, 1-nitro, 3-methoxy, or 4-propoxy; and, provided that when n is 3, $R_1$ are both H, and R are all H, $X_1$, $X_2$, $X_3$ and $X_4$ are not 3,6-dichloro or 2-methoxy-6-chloro.

A further preferred group of compounds are those compounds below falling within the scope of formula (IA) or pharmaceutically acceptable salts thereof:

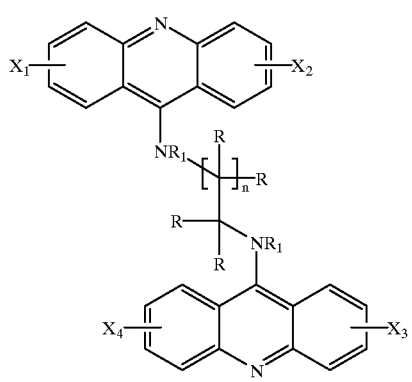

Formula (IA)

wherein:

X$_1$, X$_2$, X$_3$ and X$_4$ are independently H, optionally substituted C$_{1-6}$alkyl, C$_{3-7}$cycloalkyl-C$_{0-4}$alkyl, Ar-C$_{0-4}$alkyl, CH$_2$NR'$_2$, CH$_2$OR', CN, COR', CONR'$_2$, CO$_2$R', CF$_3$, N(R')$_2$, NR'COR', NR'CONR'R', NR'CO$_2$R'', NR'SO$_2$R'', NO$_2$, OR', S(O)$_{0-2}$R'', S(O)$_{0-2}$CF$_3$, or halo;

R' is H, optionally substituted C$_{1-6}$alkyl, C$_{3-7}$cycloalkyl-C$_{0-4}$alkyl or Ar-C$_{0-4}$alkyl;

R'' is C$_{1-6}$alkyl, C$_{3-7}$cycloalkyl-C$_{0-4}$alkyl or Ar-C$_{0-4}$alkyl;

R$_1$ are independently H, C$_{1-6}$alkyl, or one of R$_1$ is —C(O)CF$_3$;

n is 0, 1, 2 or 3; and

R is H or C$_{1-6}$alkyl, provided that when n is 1, 2 or 3, R$_1$ are both H, and R are all H, X$_1$, X$_2$, X$_3$ and X$_4$ are not all hydrogen; and, provided that when n is 1, R$_1$ are both H, and one of R is methyl, X$_1$, X$_2$, X$_3$ and X$_4$ are not all hydrogen; and, provided that when n is 1, R$_1$ are both H, R are all H, and X$_2$ and X$_3$ are each hydrogen, X$_1$ and X$_4$ are not each 4-ethyl, 3-methoxy or 4butoxy; and, provided that when n is 1, R$_1$ are both H, and R are all H, X$_1$, X$_2$, X$_3$ and X$_4$ are not 2-methoxy-6-chloro; and, provided that when n is 2, R$_1$ are both H, R are all H, and X$_2$ and X$_3$ are each hydrogen, X$_1$ and X$_4$ are not each 1-NO$_2$; and, provided that n is 2, R$_1$ are both H, and R are all H, X$_1$, X$_2$, X$_3$ and X$_4$ are not 2-methoxy-6-chloro or 2-fluoro-6-chloro; and, provided that when [C(R)$_2$]$_n$C(R)$_2$ is CH$_2$C(CH$_3$)$_2$CH$_2$, X$_1$, X$_2$, X$_3$ and X$_4$ are not 2-methoxy-6-chloro; and, provided that when n is 3, R$_1$ are both H, R are all H, and X$_2$ and X$_3$ are each hydrogen, X$_1$ and X$_4$ are not each 4-ethyl, 1-nitro, 3-methoxy, or 4-propoxy; and, provided that when n is 3, R$_1$ are both H, and R are all H, X$_1$, X$_2$, X$_3$ and X$_4$ are not 3,6-dichloro or 2-methoxy-6-chloro.

Yet another preferred group of compounds are those compounds below falling within the scope of formula (IA) or pharmaceutically acceptable salts thereof:

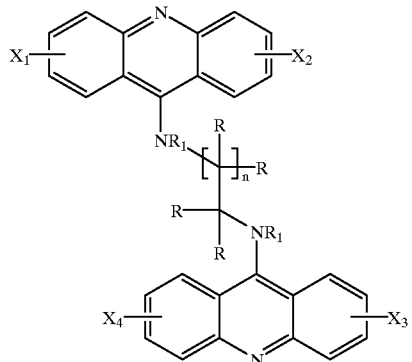

Formula (IA)

wherein:

X$_1$, X$_2$, X$_3$ and X$_4$ are independently one or more of H, OR', or halo;

R' is H or optionally substituted C$_{1-6}$alkyl;

R$_1$ is H, C$_{1-6}$alkyl, or one of R$_1$ is —CO(CF$_3$);

n is 1 or 2; and

R is H or C$_{1-6}$alkyl, provided that when R$_1$ are both H, X$_1$, X$_2$, X$_3$ and X$_4$ are not all hydrogen; and provided that when n is 1, R$_1$ are both H, and X$_2$ and X$_3$ are each hydrogen, X$_1$ and X$_4$ are not each 4-ethyl, 3-methoxy, 4butoxy; and, provided that when n is 1, and R$_1$ are both H, X$_1$, X$_2$, X$_3$ and X$_4$ are not 2-methoxy-6-chloro; and, provided that when n is 2, and R$_1$ are both H, X$_1$, X$_2$, X$_3$, and X$_4$ are not 2-methoxy-6-chloro or 2-fluoro-6-chloro.

An even more preferred group of compounds are those compounds below falling within the scope of formula (IA) or pharmaceutically acceptable salts thereof:

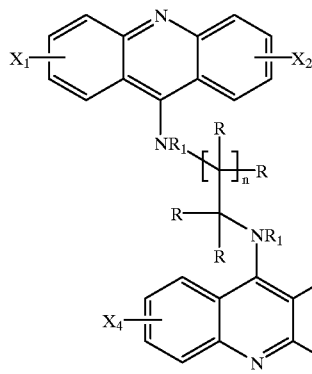

Formula (IA)

wherein:

X$_1$, X$_2$, X$_3$ and X$_4$ are independently one or more of H, OR', or halo;

R' is H or C$_{1-6}$alkyl optionally substituted with N(CH$_3$)$_2$ or CO$_2$C$_{1-6}$alkyl;

R$_1$ is H, CH$_3$, or one of R$_1$ is —CO(CF$_3$);

n is 1 or 2; and

R is H, provided that when R$_1$ are both H, X$_1$, X$_2$, X$_3$ and X$_4$ are not all hydrogen; and, provided that when n is 1, R$_1$ are both H, and X$_2$ and X$_3$ are each hydrogen, X$_1$ and X$_4$ are not each 4-ethyl, 3-methoxy, 4-butoxy, and, provided that when n is 1, and $R_1$ are both H, $X_1$, $X_2$, $X_3$ and $X_4$ are not 2-methoxy-6-chloro; and, provided that when n is 2, and $R_1$ are both H, $X_1$, $X_2$, $X_3$, and $X_4$ are not 2-methoxy-6-chloro or 2-fluoro-6-chloro.

A particularly preferred group of compounds are those compounds below falling within the scope of formula (IA) or pharmaceutically acceptable salts thereof:

Formula (IA)

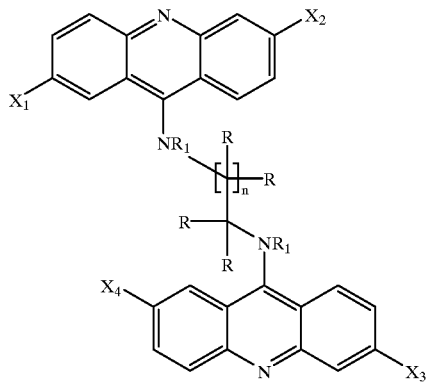

wherein:

$X_1$, $X_2$, $X_3$ and $X_4$ are independently one or more of H, OR', or halo;

R' is H or $C_{1-6}$alkyl optionally substituted with $N(CH_3)_2$, or $CO_2C_{1-6}$alkyl;

$R_1$ is H, $CH_3$, or one of $R_1$ is —$CO(CF_3)$;

n is 1 or 2; and

R is H, provided that when $R_1$ are both H, $X_1$, $X_2$, $X_3$ and $X_4$ are not all hydrogen; and, provided that when n is 1, $R_1$ are both H, and $X_2$ and $X_3$ are each hydrogen, $X_1$ and $X_4$ are not each 4-ethyl, 3-methoxy, 4-butoxy; and, provided that when n is 1, and $R_1$ are both H, $X_1$, $X_2$, $X_3$ and $X_4$ are not 2-methoxy-6-chloro; and, provided that when n is 2, and $R_1$ are both H, $X_1$, $X_2$, $X_3$, and $X_4$ are not 2-methoxy-6-chloro or 2-fluoro-6-chloro.

This invention also includes methods for preparing the novel compounds of formula (I) as follows.

Specifically covered is a method for preparing a compound of formula (I), wherein D and D' are N, and V and V' are $NR^1$ which comprises:

a) treating about two equivalents of a compound of formula (II):

Formula (II)

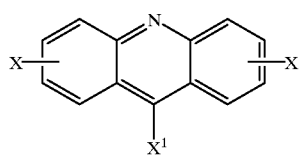

wherein where $X^1$ is a suitable leaving group, for example chloro, phenoxy, ethoxy, or bromo, with a compound of formula (III):

Formula (III)

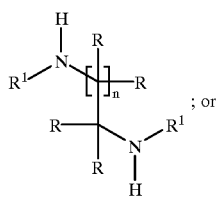

b) reacting a compound of formula (II) with a compound of formula (III) to provide a compound of formula (IV):

Formula (IV)

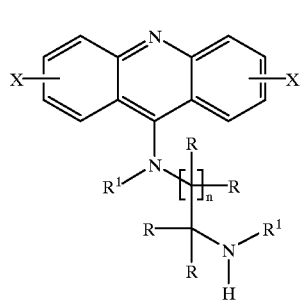

and then reacting the compound of formula (IV) with the same of different compound of formula (II); or c) (i) reacting a compound of formula (II) with a compound of formula (V):

Formula (V)

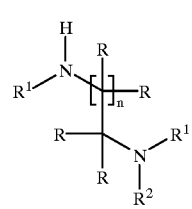

wherein $R^2$ is a suitable protecting group, for example benzyl or benzyloxycarbonyl, to provide a compound of formula (VI):

Formula (VI)

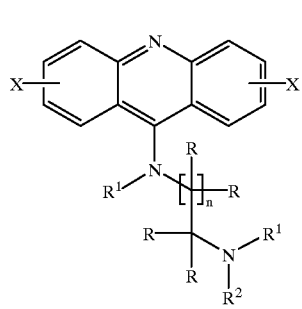

(ii) removing protecting group $R^2$ to provide a compound of formula (IV); and (iii) reacting the compound of formula (IV) with a compound of formula (II) to provide a compound of formula (I), wherein X, R, n and $R^1$ are as defined above for formula (I).

It will be understood that preferred compounds of formula (IA) may be made by analogous processes by varying the substituents on the staring materials.

Formulation of Pharmaceutical Compositions

The pharmaceutically effective compounds of this invention (and the pharmaceutically acceptable salts thereof) are administered in conventional dosage forms prepared by combining a compound of formula (I) ("active ingredient") in an amount sufficient to treat asthma and atopic disorders (for example, atopic dermatitis and allergies), rheumatoid arthritis, atherosclerosis, psoriasis, autoimmune diseases such as multiple sclerosis, inflammatory bowel disease, and HIV infection, with standard pharmaceutical carriers or diluents according to conventional procedures well known in the art These procedures may involve mixing, granulating and compressing or dissolving the ingredients as appropriate to the desired preparation.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl monostearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg to about 1000 mg. When a liquid carrier is used, the preparation will be in the form of a syrup, emulsion, soft gelatin capsule, sterile injectable liquid such as an ampule or nonaqueous liquid suspension.

The active ingredient may also be administered topically to a mammal in need of treatment of CCR5 mediated disease states. Thus, the active ingredient may be administered topically in the treatment or prophylaxis of CCR5 mediated disease states, including, but not limited to, asthma and atopic disorders (for example, atopic dermatitis and allergies), rheumatoid arthritis, atherosclerosis, psoriasis, autoimmune diseases such as multiple sclerosis, inflammatory bowel disease, and HIV infection.

The amount of active ingredient required for therapeutic effect on topical administration will, of course, vary with the compound chosen, the nature and severity of the disease state being treated and the mammal undergoing treatment, and is ultimately at the discretion of the physician. A suitable dose of an active ingredient is 1.5 mg to 500 mg for topical administration, the most preferred dosage being 1 mg to 100 mg, for example 5 to 25 mg administered two or three times daily.

By topical administration is meant non-systemic administration and includes the application of the active ingredient externally to the epidermis, to the buccal cavity and instillation of such a compound into the ear, eye and nose, and where the compound does not significantly enter the blood stream. By systemic administration is meant oral, intravenous, intraperitoneal and intramuscular administration.

While it is possible for an active ingredient to be administered alone as the raw chemical, it is preferable to present it as a pharmaceutical formulation. The active ingredient may comprise, for topical administration, from 0.001% to 10% w/w, e.g. from 1% to 2% by weight of the formulation although it may comprise as much as 10% w/w but preferably not in excess of 5% w/w and more preferably from 0.1% to 1% w/w of the formulation.

The topical formulations of the present invention, both for veterinary and for human medical use, comprise an active ingredient together with one or more acceptable carrier(s) therefor and optionally any other therapeutic ingredient(s). The carrier(s) must be 'acceptable' in the sense of being compatible with the other ingredients of the formulation and not deleterious to the recipient thereof.

Formulations suitable for topical administration include liquid or semi-liquid preparations suitable for penetration through the skin to the site of inflammation such as liniments, lotions, creams, ointments or pastes, and drops suitable for administration to the eye, ear or nose.

Drops according to the present invention may comprise sterile aqueous or oily solutions or suspensions and may be prepared by dissolving the active ingredient in a suitable aqueous or alcoholic solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98–100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol. The formulation may incorporate any suitable surface active agent such as an anionic, cationic or non-ionic surfactant such as esters or polyoxyethylene derivatives thereof. Suspending agents such as natural gums, cellulose derivatives or inorganic materials such as silicaceous silicas, and other ingredients such as lanolin, may also be included.

The active ingredient may also be administered by inhalation. By "inhalation" is meant intranasal and oral inhalation administration. Appropriate dosage forms for such administration, such as an aerosol formulation or a metered dose inhaler, may be prepared by conventional techniques. The daily dosage amount of the active ingredient administered by inhalation is from about 0.1 mg to about 100 mg per day, preferably about 1 mg to about 10 mg per day.

In one aspect, this invention relates to a method of treating asthma and atopic disorders (for example, atopic dermatitis and allergies), rheumatoid arthritis, atherosclerosis, psoriasis, autoimmune diseases such as multiple sclerosis, inflammatory bowel disease, and HIV infection, all in mammals, preferably humans, which comprises administering to such mammal an effective amount of a CCR5 receptor ligand, in particular, an antagonist as depicted in formula (I).

By the term "treating" is meant either prophylactic or therapeutic therapy. Such formula (I) compound can be administered to such mammal in a conventional dosage form prepared by combining the formula (I) compound with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables. The formula (I) compound is administered to a mammal in need of treatment for asthma and atopic disorders (for example, atopic dermatitis and allergies), rheumatoid arthritis, atherosclerosis, psoriasis, autoimmune diseases such as multiple sclerosis, inflammatory bowel disease, and HIV infection, in an amount sufficient to decrease symptoms associated with these disease states. The route of administration may be oral or parenteral.

The term parenteral as used herein includes intravenous, intramuscular, subcutaneous, intra-rectal, intravaginal or intraperitoneal administration. The subcutaneous and intramuscular forms of parenteral administration are generally preferred. The daily parenteral dosage regimen will preferably be from about 30 mg to about 300 mg per day of active ingredient. The daily oral dosage regimen will preferably be from about 100 mg to about 2000 mg per day of active ingredient.

It will be recognized by one of skill in the art that the optimal quantity and spacing of individual dosages of a formula (I) compound will be determined by the nature and extent of the condition being treated, the form, route and site of administration, and the particular mammal being treated, and that such optimums can be determined by conventional techniques. It will also be appreciated by one of skill in the art that the optimal course of treatment, i.e., the number of doses of the formula (I) compound given per day for a defined number of days, can be ascertained by those skilled in the art using conventional course of treatment determination tests.

Methods of Preparation

The compounds of formula (I) can be prepared by art-recognized procedures from known or commercially available starting materials. If the starting materials are unavailable from a commercial source, their synthesis is described herein, or they can be prepared by procedures known in the art.

Specifically, compounds of formula (I) where D and D' are N, and V and V' are NR$^1$ are prepared according to the general method of Scheme I from suitably substituted acridines 1-1, where X$^1$ is a suitable leaving group, for example chloro, phenoxy, ethoxy, or bromo, and X are as defined in Formula (I). Substituted acridines 1-1 are known to the art and may be prepared by methods known to the art, for example, see "The Acridines", Second Edition, William Clowes and Sons, London, 1966; "Acridines", 2nd ed., Acheson, R. M., Ed., Interscience Publishers, New York, 1973, Chapter 1; *Heterocycles* 1977, 6(7) 987–1060; and *J. Med. Chem.* 1978, 21, 868–874.

Compound 1-1 is treated with a suitably substituted diamine, 1-2, where n, R, and R$^1$ are as defined in formula (I); diamines 1-2 are known to the art and may be prepared by methods known to the art.

For example, approximately two equivalents of a suitably substituted acridine 1-1 is treated with a suitably substituted diamine 1-2 in a suitable solvent, for example phenol or 1-methyl-2-pyrrolidinone, at a suitable temperature, for example 25–180° C., for a suitable time, for example 1–4 hours, to give 1-4, as described in *J. Am. Chem. Soc.* 1947, 69, 468; *J. Med. Chem.* 1978, 21, 658–668; and *J. Med. Chem.* 1978, 21, 868–874.

Alternatively, 1-4 may be obtained in two steps by reacting 1-1 with 1-2 to afford 1-3 which is then reacted with the same or different 1-1 to afford 1-4.

Alternatively, 1-3 may be heated in a suitable solvent, for example dimethyl sulfoxide, at a suitable temperature, for example 130° C., for a suitable time, for example four days, to afford 1-4.

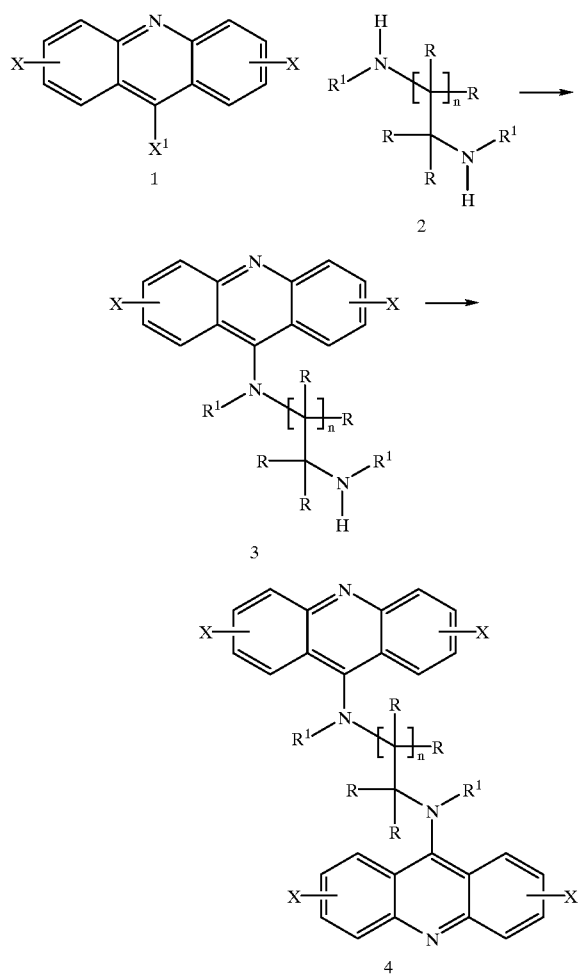

Scheme 1

Alternatively, using the general method of Scheme 1, one may replace 1-2 with 1-2' in which R$^2$ is a suitable protecting group, for example benzyl or benzyloxycarbonyl. Reaction of 1-1 and 1-2' affords 1-3'; removal of the protecting group R$^2$ from 1-3' using conditions known to the art affords 1-3 which is then reacted with 1-1 to afford 1-4.

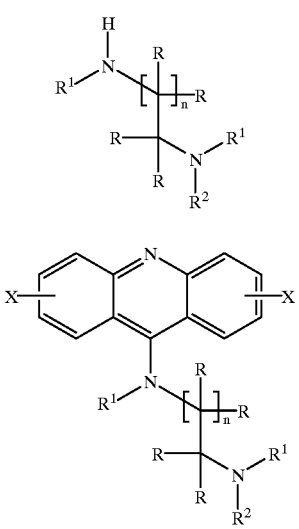

Compounds of formula (I) where D and D' are N, V is NR[1], and V' is S, are prepared according to the general method of Scheme 1 except replacing diamine 1-2 with amino-mercaptan 2-2 as shown in Scheme 2.

Compound 2-1 is treated with a suitably substituted amino-mercaptan, 2-2, where n, R, and R[1] are as defined in formula (I); amino-mercaptans 2-2 are known to the art and may be prepared by methods known to the art.

For example, approximately two equivalents of 2-1 are heated with 2-2 in a suitable solvent, for example phenol, at a suitable temperature, for example 80° C., for a suitable time, for example 3 hours, to afford 2-3 as described in *Tetrahedron* 1989, 45, 6455–66.

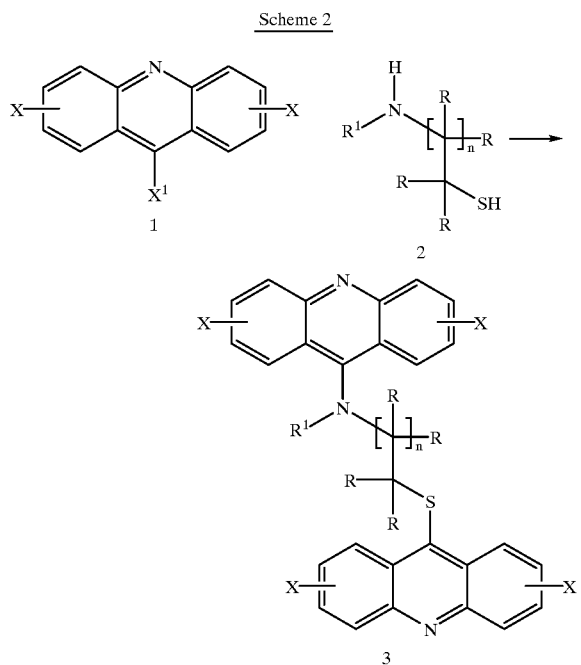

Compounds of formula (I) where D and D' are N, and V and V' are S are prepared according to the method of Scheme 3 from substituted 9-(mercapto)acridines 3-1 where X are as defined in Formula (I). 9-(Mercapto)acridines 3-1, which may also exist as their tautomeric 10H-acridine-9-thiones, are known to the art and are prepared by methods known to the art.

Compounds 3-1 are reacted with compounds 3-2 where $X^2$ are independently, suitable leaving groups such as chloro, bromo, iodo, mesyloxy, or tosyloxy, and n and R are as defined in formula (I), to give 3-3. Compounds 3-2 are known to the art and are prepared by methods known to the art.

For example, approximately two equivalents of 3-1 is treated with 3-2 in a suitable solvent, for example toluene, and a suitable base, for example 50% aqueous potassium hydroxide, at a suitable temperature, for example at reflux, for a suitable time, for example 2 hours, to afford 3-3, as described in *Eur. J. Med. Chem.* 1991, 26, 117–9.

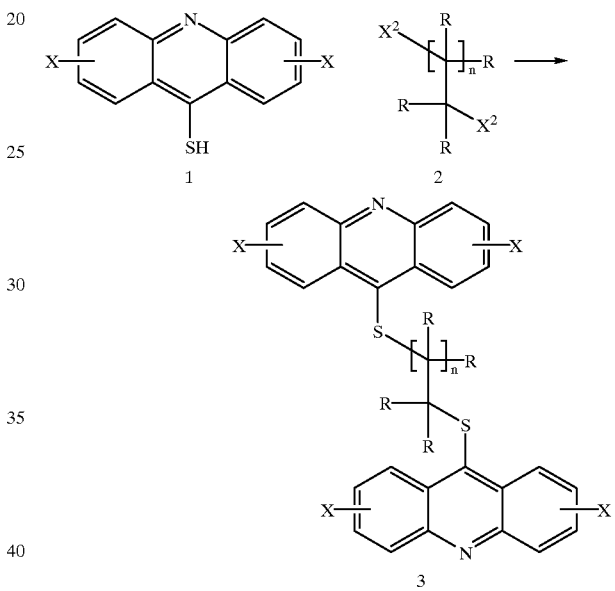

Compounds of formula (I) where D and D' are CX, and V and V' are O are prepared by the general method of Scheme 4 from suitably substituted 9-(hydroxy)anthracenes 4-1 where X are as defined in formula (I). Substituted 9-(hydroxy)anthracenes 4-1, which may also exist as their tautomeric anthrones, are known to the art and may be prepared by methods known to the art.

Compounds 4-1 are reacted with compounds 4-2 where $X^2$ are independently, suitable leaving groups such as chloro, bromo, iodo, mesyloxy, or tosyloxy, and n and R are as defined in formula (I), to give 4-4. Compounds 4-2 are known to the art and are prepared by methods known to the art.

For example, a suitably substituted 9-(hydroxy)anthracene 4-1 is treated with 4-2 in a suitable solvent, for example dichloromethane, and a suitable base, for example aqueous sodium hydroxide, and a suitable phase transfer agent, for example tetrabutylammonium hydroxide, at a suitable temperature, for example at reflux, for a suitable time, for example eleven days to afford 4-3. Treatment of 4-3 with the same or different 4-1 using similar conditions affords 4-4 as described in *J. Chem. Soc. Perkin Trans. II* 1988, 1885–1894.

Scheme 4

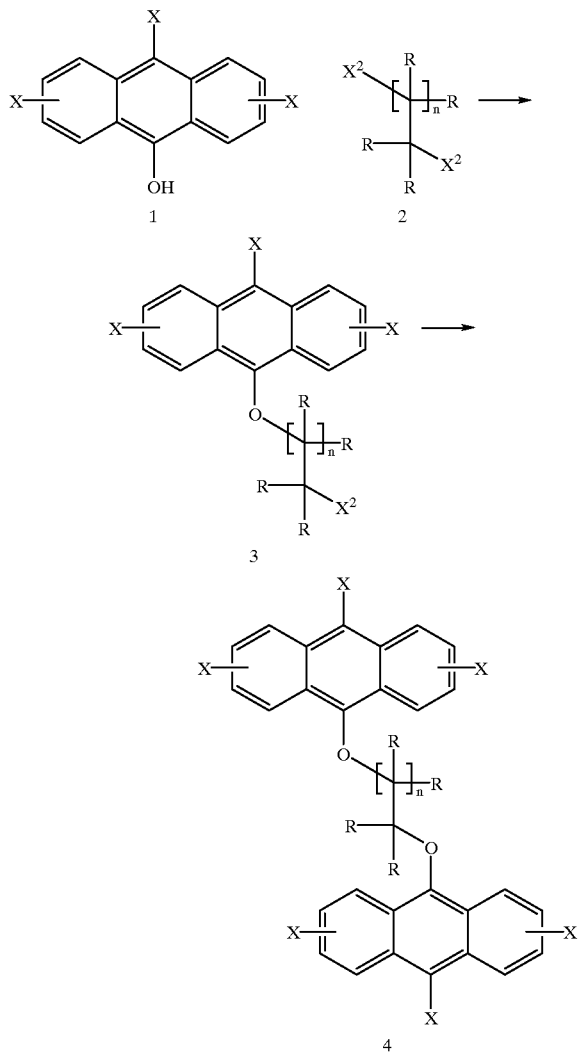

Scheme 5

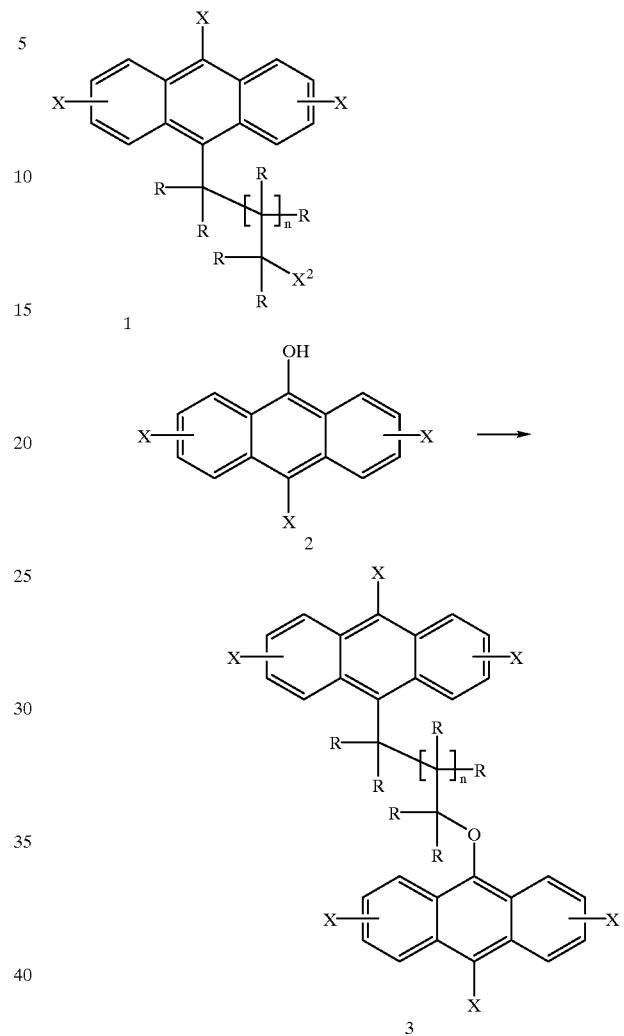

Compounds of formula (I) where D and D' are CX, V is $C(R)_2$ and V' is O are prepared according to the method of Scheme 5 from suitably substituted anthracine 5-1, where $X^2$ is a suitable leaving group such as chloro, bromo, iodo, mesyloxy or tosyloxy, and X, R, and n are as defined in Formula (I). Substituted anthracines 5-1 are known to the art and may be prepared by methods known to the art.

Compound 5-1 is treated with a suitably substituted 9-(hydroxy)anthracine, 5-2, where X are as defined in Formula (I); 9-(hydroxy)anthracines 5-2 are known to the art and may be prepared by methods known to the art.

For example, 5-1 and 5-2 are reacted in a suitable solvent, for example tetrahydrofuran, and a suitable base, for example aqueous sodium hydroxide, at a suitable temperature, for example at reflux, for a suitable time, for example 4 hours to afford 5-3 as described in *J. Chem. Soc. Perkin Trans. II* 1988, 1885–1894.

Compounds of formula (I) where D and D' are CX, and V and $V^1$ are $CR_2$ are prepared according to the method of Scheme 6 from suitably substituted dihydro-anthracines 6-1 where X are as defined in formula (I). Substituted anthracines 6-1 are known to the art and may be prepared by methods known to the art.

Compound 6-1 is treated with a suitably substituted 6-2, where $X^2$ are independently, suitable leaving groups, for example chloro, bromo, iodo, mesyloxy or tosyloxy, and n and R are as defined in Formula (I). Compounds 6-2 are known to the art and may be prepared by methods known to the art.

For example, 6-1 is reacted in a suitable solvent, for example tetrahydrofuran, with a suitable base, for example n-butyllithium, treated with 6-2, and then with a suitable oxidant, for example 2,3-dichloro5,6-dicyano-1,4-benzoquinone, to afford 6-3 as described in *J. Chem. Soc. Perkin Trans II* 1988, 1885–1894.

Alternatively, 6-3 may be prepared from a suitably substituted anthrone and a bis-Grignard as described in *J. Am. Chem. Soc.* 1980, 102, 3524–3530.

Scheme 6

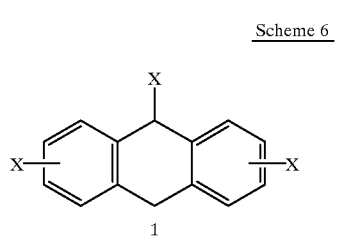

Scheme 7

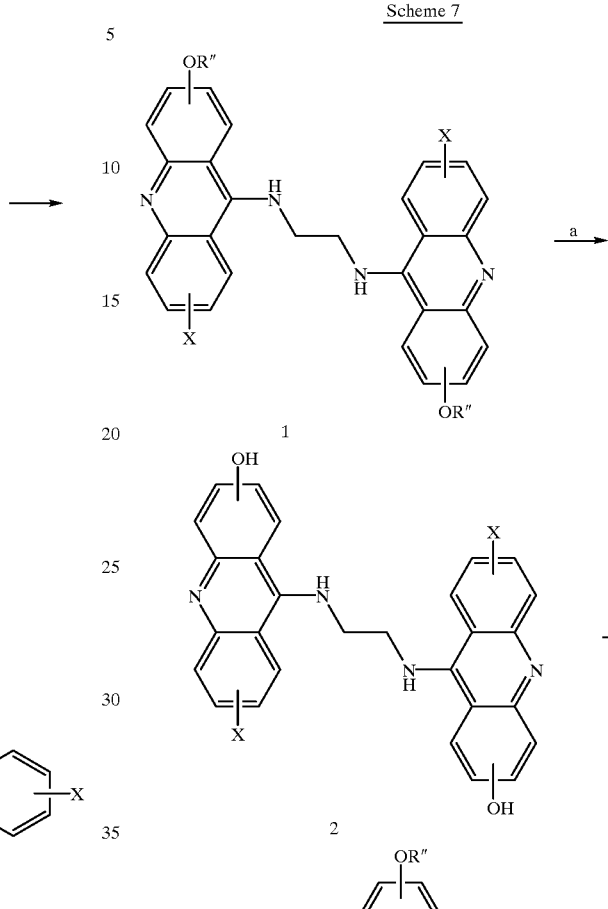

Compounds of formula (I) where one or more X is OR' are also prepared according to the general method of Scheme 7. For example, a compound of S formula (I) where one or more X is OR" and R" is optionally substituted $C_{1-6}$alkyl, $C_{3-7}$cycloalkyl-$C_{0-4}$alkyl or Ar-$C_{0-4}$alkyl, e.g., 7-1, is reacted with 4 to 10 equivalents of methionine or a suitable sulfur nucleophile in a suitable solvent, for example methanesulfonic acid, at a suitable temperature, for example 85° C., for a suitable time, for example 4–18 hours, to give a compound of formula (I) where one of more X is OH, e.g., 7-2.

Further, for example, 7-2 is treated with a suitable reagent R"$X^2$, where R" is optionally substituted $C_{1-6}$alkyl, $C_{3-7}$cycloalkyl-$C_{0-4}$alkyl or Ar-$C_{0-4}$alkyl, and $X^2$ is a suitable leaving group such as chloro, bromo, iodo, mesyloxy, or tosyloxy, in the presence of a suitable base, for example sodium hydride or potassium carbonate, in a suitable solvent, for example dimethylsulfoxide or dimethylformamide, at a suitable temperature, for example 85° C., for a suitable time, for example 4–18 hours, to give compounds of formula (I) where one or more X is OR", e.g., 7-3. Reagents defined by R"$X^2$ are known to the art or may be prepared by methods known to the art.

Reagents: (a) methionine, $CH_3SO_3H$; (b) DMSO, NaH or DMF, $K_2CO_3$, R"$X^2$.

Compounds of formula (I) where D and D' are N, V and V' are $NR^1$ and one or more of $R^1$ is acyl are prepared by the general method of Scheme 8. For example, 8-1, is reacted with a suitable acylating agent, for example trifluoroacetic anhydride, and a suitable base, for example triethylamine, in a suitable solvent, for example dichloromethane, at a suitable temperature, for example 25° C., for a suitable time, for example, 18 hours, to give 8-2.

Scheme 8

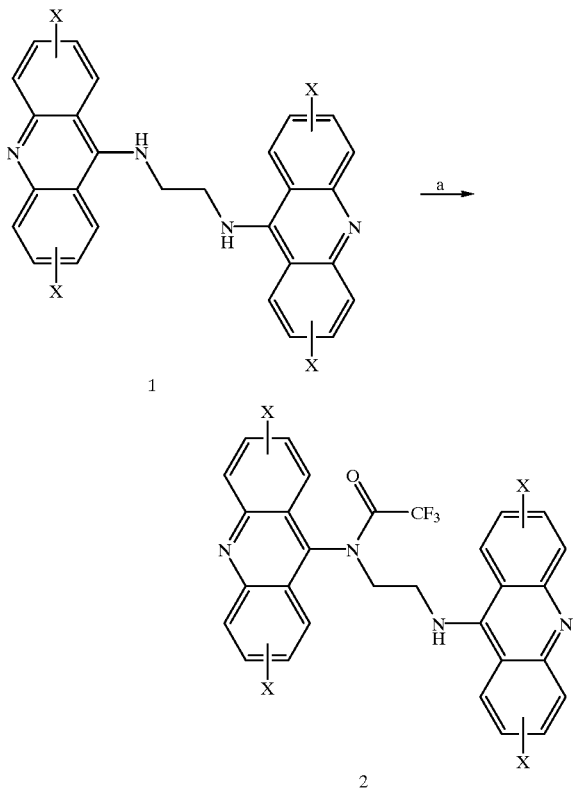

Reagents: (a) (CF$_3$CO)$_2$O, Et$_3$N, CH$_2$Cl$_2$.

Compounds of formula (I) where D and D' are N, V and V' are NR$^1$, and R$^1$ is optionally substituted C$_{1-6}$alkyl, C$_{3-7}$cycloalkyl-C$_{0-4}$alkyl or Ar-C$_{0-4}$alkyl are prepared by the general method of Scheme 9. For example, 9-1 is treated with a suitable base, for example sodium hydride, in a suitable solvent, for example dimethylsulfoxide, and a suitable alkylating agent, for example iodomethane, at a suitable temperature, for example 75° C., for a suitable time, for example 1–2 hours, to give 9-2.

Scheme 9

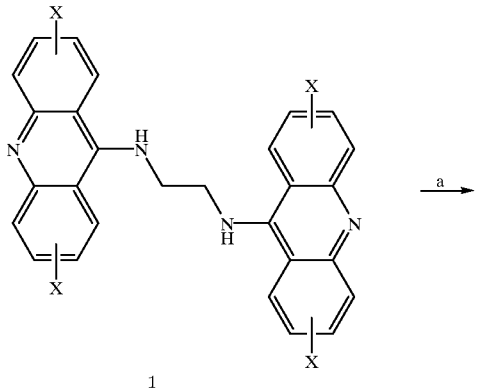

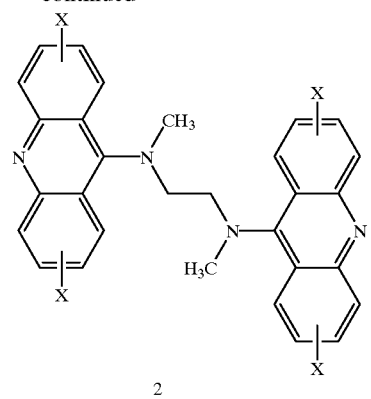

Reagents: (a) DMSO, NaH, CH$_3$I.

Compounds of formula (I) where D and D' are N, V and V' are CH$_2$, and n is 0 are prepared according to the general method of Scheme 10. For example, 10-1, where X$^1$ is a suitable leaving group, for example chloro, phenoxy, ethoxy, or bromo, is converted to malonate 10-2 by reaction with a suitable malonate ester, for example diethyl malonate, in the presence of a suitable base, for example sodium ethoxide, in a suitable solvent mixture, for example ethanol and toluene, at a suitable temperature, for example 85–100° C., for a suitable time, for example 16 hours. The resulting malonate is hydrolyzed in with a suitable reagent, for example hydrochloric acid, at a suitable temperature, for example 100–120° C., for a suitable time, for example 4 hours to give 10-2, using the general method of *J. Med. Chem.* 1969, 12, 913.

Further, for example, reaction of 10-2 with a suitable aldehyde, for example paraformaldehyde, and a suitable secondary amine hydrochloride, for example dimethylamine hydrochloride, in a suitable solvent, for example ethanol, at a suitable temperature, for example 75–85° C., for a suitable time, for example 2 hours gives compounds of formula 10-3, using the general procedure of *Bull. Chem. Soc. Japan*, 1972, 45, 3187.

Scheme 10

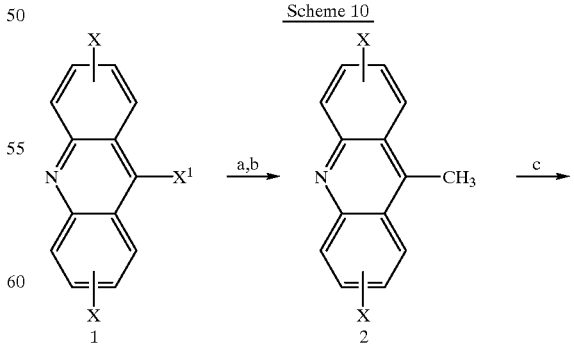

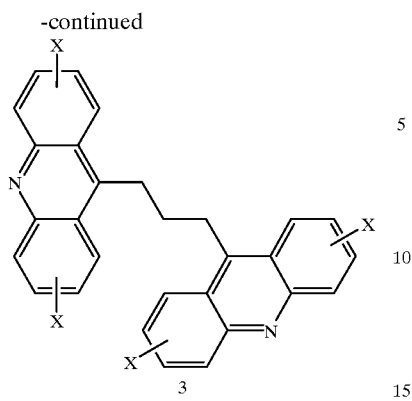

Reagents: (a) diethyl malonate/Na/EtOH; (b) conc. HCl/H$_2$O; (c) paraformaldehyde/dimethylamine HCl.

Compounds of formula (I) where D and D' are N, V and V' are C(R)$_2$, R is H, and n is 2 are prepared according to the general method of Scheme 11. For example, compounds 11-1, where X$^1$ is a suitable leaving group, for example chloro, phenoxy, ethoxy, or bromo, are treated with a suitable alkynol, for example 2-methyl-3-butyn-2-ol, in the presence of a suitable palladium catalyst, for example bis(triphenylphosphine)palladium dichloride, in a suitable solvent mixture, for example triethylamine and dimethylformamide, at a suitable temperature, for example 90° C., for a suitable time, for example 18 hours to give an intermediate alkynol. The alkynol is heated to reflux in the presence of a suitable base, for example solid NaOH, in a suitable solvent, for example toluene, at a suitable temperature, for example 120–150° C., for a suitable time, for example 2 hours, to give 11-2 using the general procedure of *J. Het. Chem.*, 1984, 21, 607.

Compounds 11-2 are treated with a suitable palladium catalyst, for example bis(triphenylphosphine)palladium dichloride, CuI, and a suitable oxidant, for example I$_2$, in a suitable solvent mixture, for example diisopropylamine and dimethylformamide, at a suitable temperature, for example 25° C., for a suitable time, for example 2 hours. The resulting diyne 11-3 is hydrogenated in an atmosphere of hydrogen gas in the presence of a suitable catalyst, for example 10% palladium on carbon, in a suitable solvent mixture, for example ethyl acetate and methanol, at a suitable temperature, for example 25° C., for a suitable time, for example 18 hours, to give 11-4 using the general method of *Tet. Lett.*, 1997, 4371.

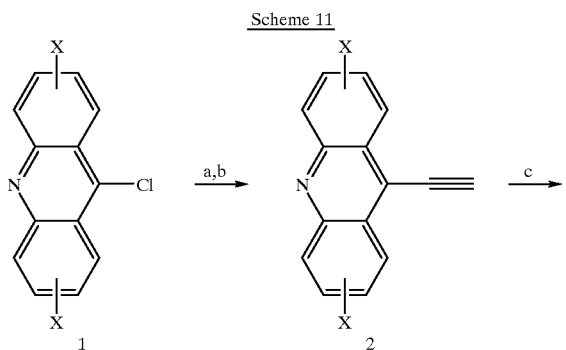

Scheme 11

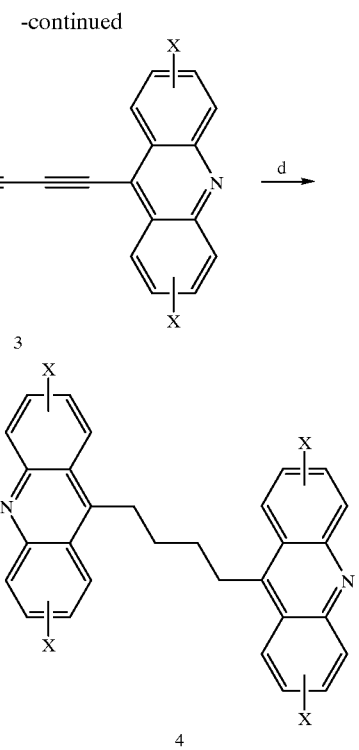

Reagents: (a) 2-methyl-3-butyn-2-ol/Pd(PPh$_3$)$_2$Cl$_2$/DMF/TEA; (b) NaOH/toluene; (c) Pd(PPh$_3$)$_2$Cl$_2$/CuI/I$_2$/DMF/i-propylamine, (d) H$_2$, 10% Pd/C, MeOH, EtOAc.

Experimentals

EXAMPLE 1

Preparation of N,N'-bis(6-chloro-2-methoxy-9-acridinyl)-1,2-ethanediamine bis(trifluoroactate)

N-(6-Chloro-2-methoxy-9-acridinyl)-1,2-ethanediamine (250 mg) (*Tetrahedron Lett.* 1995, 36, 6651–4) was dissolved in DMSO and heated to 130° C. for 4 d. The mixture was diluted with ethyl acetate and washed with water. The resulting precipitate was filtered, dried, and purified by MPLC (YMC ODS-AQ, 20% acetonitrile/water-0.1% trifluoroacetic acid) to afford the title compound. MS(ES) m/e 543.1(M+H)$^+$; mp 220–225° C. (decomposition).

EXAMPLE 2

Preparation of N,N'-bis(6-chloro-2-methoxy-9-acridinyl)-1,2-ethanediamine bis(trifluoroactate)

A mixture of 6,9-dichloro-2-methoxyacridine (7 g, 25.3 mmol), ethylenediamine (0.8 mL, 12.6 mmol), and triethylamine (3.5 mL, 25.3 mmol) in 1-methyl-2-pyrrolidinone (35 mL) was heated at 130° C. for 2 h. The resulting suspension was filtered to give the title compound, which was triturated in hot ethanol and dried (3.8 g). MS(ES) m/e 543.1 (M+H)$^+$.

EXAMPLE 3

Preparation of N,N'-di-9-acridinyl-1,2-ethanediamine bis(trifluoroacetate)

9-Chloroacridine (1 g, 4.68 mmol), ethylenediamine (0.16 mL, 2.34 mmol), and diisopropylethylamine (1.63 mL, 9.36 mmol) in phenol (5 g) were stirred at 115° C. for 3 h. The reaction was cooled and concentrated hydrochloric acid (4 mL) was added followed by ether (10 mL). The resulting precipitate was filtered, triturated with 30% aqueous sodium hydroxide (10 mL), filtered again, washed with water, and dried under vacuum at 50° C. overnight. A portion of the resulting solid was purified by MPLC (YMC ODS-AQ, 20% acetonitrile/water-0.1% trifluoroacetic acid) and a portion of the resulting solid was further purified by HPLC (YMC ODS-AQ, 100×250 mm, 80 mL/min, gradient, A:acetonitrile B:water-0.1% trifluoroacetic acid, 10–50% during 20 min, UV detection at 254 nm) to give the desired compound as a yellow solid. MS(ES) m/e 415.3(M+H)$^+$; mp 225–230° C. (decomposition).

EXAMPLE 4

Preparation of N,N'-bis(6-chloro-2-methoxy-9-acridinyl)-1,3-propanediamine bis(trifluoroactate)

A mixture of 6,9-dichloro-2-methoxyacridine (0.56 g, 2 mmol), 1,3-diaminopropane (0.08 mL, 1 mmol), and triethylamine (0.28 mL, 1 mmol) in 1-methyl-2-pyrrolidinone (5 mL) was heated at 130° C. for 2 h. The resulting solid was filtered and purified by HPLC (YMC ODS-AQ, 100×250 mm, 80 mL/min, 20% acetonitrile/water-0.1% trifluoroacetic acid, UV detection at 254 nm) to give the title compound as a yellow solid. MS(ES) m/e 557.2 (M+H)$^+$.

EXAMPLE 5

Preparation of 9.9'-(1,4-piperazinediyl)bis[6chloro-2-methoxy-acridine]bis(trifluoroacetate)

A mixture of 6,9-dichloro-2-methoxyacridine (0.56 g, 2 mmol), piperazine (0.086 g, 1 mmol), and triethylamine (0.28 mL, 1 mmol) in 1-methyl-2-pyrrolidinone (5 mL) was heated at 130° C. for 2 h. The resulting solid was triturated with a mixture of acetic acid and trifluoroacetic acid to give the title compound as a yellow solid. MS(ES) m/e 569.1 (M+H)$^+$.

EXAMPLE 6

Preparation of N-(6-chloro-2-methoxy-9-acridinyl)-N'-(6-chloro-2-hydroxy-9-acridinyl]-1,2-ethanediamine bis(trifluoroacetate)

A mixture of N,N'-bis(6-chloro-2-methoxy-9-acridinyl)-1,2-ethanediamine (0.54 g, 1.0 mmol) and DL-methionine (1.2 g, 8.0 mmol) in methanesulfonic acid (8.0 mL) was heated at 85° C. for 16 h. The reaction was cooled and basified with cold ammonium hydroxide to pH 7.5. The resulting red solid was filtered and purified by HPLC(YMC ODS-AQ, 100×250 mm, 80 mL/min, 28% acetonitrile/water-0.1% trifluoroacetic acid, UV detection at 254 nm) and a portion of the resulting solid was further purified by HPLC to give the title compound as a yellow solid. MS(ES) m/e 529.3 (M+H)$^+$.

EXAMPLE 7

Preparation of N,N'-bis(6-chloro-2-hydroxy-9-acridinyl)-1,2-ethanediamine bis(trifluoroactate)

A mixture of N,N'-bis(6-chloro-2-methoxy-9-acridinyl)-i,2-ethanediamine (0.54 g, 1.0 mmol) and DL-methionine (1.48 g, 10.0 mmol) in methanesulfonic acid (8.0 mL) was heated at 85° C. for 16 h. The reaction was cooled and basified with cold ammonium hydroxide to pH 7.5. The resulting red solid was filtered and purified by HPLC(YMC ODS-AQ, 100×250 mm, 80 mL/min, 28% acetonitrile/water-0.1% trifluoroacetic acid, UV detection at 254 nm) and a portion of the resulting solid was further purified by HPLC to give the title compound as a yellow solid. MS(ES) m/e 515.2 (M+H)$^+$.

EXAMPLE 8

Preparation of N-[6-chloro-2-(2,2-dimethylpropoxy)-9-acridinyl]-N'-(6-chloro-2-hydroxy-9-acridinyl]-1,2-ethanediamine bis(trifluoroactate)

To a solution of DMSO (4 mL) and NaH (44 mg, 1.1 mmol) heated at 70° C. for 15 min was added N,N-bis(6-chloro-2-hydroxy-9-acridinyl)-1,2-ethanediamine (0.258 g, 0.5 mmol) and neopentyl iodide (0.22 g, 1.10 mmol). After 24 h, the reaction mixture was poured into ice water. The resulting solid was filtered and purified by HPLC (YMC ODS-AQ, 100×250 mm, 80 mL/min. 42% acetonitrile/water/0.1% trifluoroacetic acid, UV detection at 254 nm) to give the title compound as a yellow solid. MS(ES) m/e 585.2 (M+H)$^+$.

EXAMPLE 9

Preparation of N-[6-chloro-2-(2,2-dimethylpropoxy)-9-acridinyl]-N'-(6-chloro-2-methoxy-9-acridinyl]-1,2-ethanediamine bis(trifluoroactate)

A mixture of N-(6-chloro-2-methoxy-9-acridinyl)-N'-(6-chloro-2-hydroxy-9-acridinyl]-1,2-ethanediamine (0.257 g, 0.5 mmol) and neopentyl iodide (0.22 g, 1.10 mmol) in DMF (10 mL) was heated at 90° C. for 24 h. The reaction mixture was cooled and poured into ice water. The resulting solid was filtered and purified by HPLC (YMC ODS-AQ, 100× 250 mm, 80 mL/min, 48% acetonitrile/water/0.1% trifluoroacetic acid, UV detection at 254 nm) to give the title compound as a yellow solid. MS(ES) m/e 599.2 (M+H)$^+$.

EXAMPLE 10

Preparation of N,N'-bis[6chloro-2-(2,2-dimethylpropoxy)-9-acridinyl]-1,2-ethanediamine bis(trifluoroactate)

A mixture of N,N'-bis(6chloro-2-hydroxy-9-acridinyl)-1,2-ethanediamine (0.258 g, 0.5 mmol), K$_2$CO$_3$ (0.56 g, 4 mmol), and neopentyl iodide (0.8 g, 4.0 mmol) in DMF (10 mL) was heated at 90° C. for 24 h. The reaction mixture was cooled and poured into ice water. The resulting solid was filtered and purified by HPLC (YMC ODS-AQ, 100×250 mm, 80 mL/min, 50% acetonitrile/water0.1% trifluoroacetic acid, UV detection at 254 nm) to give the title compound as a yellow solid. MS(ES) m/e 655.3 (M+H)$^+$.

EXAMPLE 11

Preparation of N,N'-bis[6-chloro2-(tert-butoxycarbonyl)methoxy-9-acridinyl]-1,2-ethanediamine bis(trifluoroactate)

To a solution of DMSO (4 mL) and NaH (22 mg, 1.1 mmol) heated at 70° C. for 15 min was added N,N'-bis(6-chloro-2-hydroxy-9-acridinyl)-1,2-ethanediamine (0.129 g, 0.5 mmol)) and tert-butyl bromoacetate (0.13 g, 0.67 mmol). After 18 h, the reaction mixture was poured into ice water. The resulting solid was filtered and purified by HPLC (YMC ODS-AQ, 100×250 mm, 80 mL/min, 39% acetonitrile/

EXAMPLE 12

Preparation of [-6-chloro-2-(tert-butoxycarbonylmethoxy-9-acridinyl)-N'-[(6-chloro-2-hydroxy-9-acridinyl)-1,2-ethanediamine bis (trifluoroactate)

To a solution of DMSO (4 mL) and NaH (22 mg, 1.1 mmol) heated at 70° C. for 15 min was added N,N'-bis(6-chloro-2-hydroxy-9-acridinyl)-1,2-ethanediamine (0.129 g, 0.5 mmol) and tert butyl bromoacetate (0.13 g, 0.67 mmol). After 18 h, the reaction mixture was poured into ice water. The resulting solid was filtered and purified by HPLC (YMC ODS-AQ, 100×250 mm, 80 mL/min, 39% acetonitrile/water/0.1% trifluoroacetic acid, UV detection at 254 nm) to give the title compound as a yellow solid. MS(ES) m/e 629.4 (M+H)+.

EXAMPLE 13

Preparation of N-[6chloro-2-(tert-butoxycarbonyl)methoxy-9-acridinyl]-N'-(6-chloro-2-methoxy-9-acridinyl)-1,2-ethanediamine bis(trifluoroactate)

To a solution of DMSO (4 mL) and NaH (22 mg, 1.1 mmol) heated at 70° C. for 15 min was added of N-(6chloro-2-methoxy-9-acridinyl)-N'-(6-chloro-2-hydroxy-9-acridinyl]-1,2-ethanediamine (0.3 g, 0.6 mmol) and tert-butyl bromoacetate (0.15 g, 0.76 mmol). After 8 h, the reaction mixture was poured into ice water. The resulting solid was filtered and purified by HPLC (YMC ODS-AQ, 100×250 mm, 80 mL/min, 38% acetonitrile/water/0.1% trifluoroacetic acid, UV detection at 254 nm) to give the title compound as a yellow solid. MS(ES) m/e 643.4 (M+H)+.

EXAMPLE 14

Preparation of N,N'-bis(6chloro-2-carboxymethoxy-9-acridinyl)-1,2-ethanediamine bis(trifluoroactate)

A solution of N,N'-bis[6-chloro-2-(tert-butoxycarbonyl)methoxy-9-acridinyl]-1,2-ethanediamine (12 mg, 0.12 mmol) and trifluoroacetic acid (5 mL) in dichloromethane (12 mL) was stirred at RT for 18 h. The reaction mixture was concentrated in vacuo and the residue was purified by HPLC (YMC ODS-AQ, 100×250 mm, 80 mL/min, 26% acetonitrile/water/0.1% trifluoroacetic acid, UV detection at 254 nm) to give the title compound as a yellow solid. MS(ES) m/e 631.3 (M+H)+.

EXAMPLE 15

Preparation of N-[6chloro-2-(2-dimethylamino)ethoxy-9-acridinyl]-N'-(6-chloro-2-hydroxy-9-acridinyl]-1,2-ethanediamine bis(trifluoroactate)

To a solution of DMSO (4 mL) and NaH (22 mg, 1.1 mmol) heated at 70° C. for 15 min was added N,N'-bis(6-chloro-2-hydroxy-9-acridinyl)-1,2-ethanediamine (0.258 g, 0.5 mmol) and 2-(dimethylamino)ethyl chloride (0.317. g, 2.2 mmol). After 18 h, the reaction mixture was poured into ice water. The resulting solid was filtered and purified by HPLC (YMC ODS-AQ, 100×250 mm, 80 mL/min, 26% acetonitrile/water/0.1% trifluoroacetic acid, UV detection at 254 nm) to give the title compound as a yellow solid. MS(ES) m/e 586.3 (M+H)+.

EXAMPLE 16

Preparation of N,N'-bis[(chloro-2-methoxy-9-acridinyl)-N,N'-dimethyl-1,2-ethanediamine bis (trifluoroactate)

To a solution of DMSO (4 mL) and NaH (40 mg, 1.0 mmol) heated at 70° C. for 15 min was added N,N'-bis(6-chloro-2-methoxy-9-acridinyl)-1,2-ethanediamine (0.27 g, 0.5 mmol) followed by methyl iodide (0.06 mL, 1.0 mmol). After 1 h, the reaction mixture was poured into ice water. The resulting solid was filtered and purified by HPLC (YMC ODS-AQ, 100×250 mm, 80 mL/min, 35% acetonitrile/water/0.1% trifluoroacetic acid, UV detection at 254 nm) to give the title compound as a yellow solid. MS(ES) m/e 571.2 (M+H)+.

EXAMPLE 17

Preparation of N,N'-bis(chloro-2-methoxy-9-acridinyl)-N-(trifluoromethylcarbonyl)-1,2-ethanediamine bis(trifluoroactate)

To a suspension of N,N'-bis(6-chloro2-methoxy-9-acridinyl)-1,2-ethanediamine (0.27 g, 0.5 mmol) in dichloromethane (20 mL) was added triethyl amine (1 mL, 7 mmol) followed by trifluoroacetic anhydride (1 mL, 7.0 mmol). After 18 h, the solution was diluted with dichloromethane (100 mL), washed with water, dried and concentrated in vacuo to a yellow semi-solid, which was purified by HPLC (YMC ODS-AQ, 100×250 mm, 80 mL/min, 50% acetonitrile/water/0.1% trifluoroacetic acid, UV detection at 254 nm) to give the titled compound as a yellow solid. MS(ES) m/e 639.1 (M+H)+.

EXAMPLE 18

Preparation of N,N'-bis(6-chloro-2-methoxy-9-acridinyl)-N,N'-bis(trifluoromethylcarbonyl)-1,2-ethanediamine bis(trifluoroactate)

To a suspension of N,N'-bis(6-chloro-2-methoxy-9-acridinyl)-1,2-ethanediamine (0.157 g, 0.3 mmol) in dichloromethane (10 mL) was added triethylamine (3 mL, 20 mmol) followed by trifluoroacetic anhydride (3 mL, 20 mmol). After 18 h, the solution was diluted with dichloromethane (100 mL), washed with water, dried and concentrated in vacuo to give yellow solid, which was purified by flash column chromatography (silica gel, 1–2% methanol:dichloromethane) to give the title compound as a yellow solid. MS(ES) m/e 735.3 (M+H)+.

EXAMPLE 19

Preparation of bis(6-chloro-2-methoxy-9-acridinyl)-1,3-propane a) diethyl (6-chloro-2-methoxy-9-acridinyl)malonate To a solution of sodium (1.3 g, 52 mmol) in ethanol (50 mL) was added diethyl malonate (8.8 g 55 mmol) followed by 6,9-dichloro-2-methoxyacridine (9.68 g, 35 mmol) and toluene (5 mL). The mixture was heated to reflux for 24 h, diluted with aqueous potassium carbonate, extracted with ethyl acetate, dried, and concentrated in vacuo to give solid which was purified by flash column chromatography (silica gel, 5–12% methanol:dichloromethane) to give the title compound. MS(ES) m/e 402.2 (M+H)+.

b) 6-chloro-2-methoxy-9-methylacridine

A solution of the compound of Example 19 (a) (2.2 g, 5.5 mmol) in water (5 mL) and concentrated hydrochloric acid (Beginning of page, continuation text:)

water/0.1% trifluoroacetic acid, UV detection at 254 nm) to give the title compound as a yellow solid. MS(ES) m/e 743.4 (M+H)+.

was heated to reflux for 4 h and filtered to give the title compound. MS(ES) m/e 258.2 (M+H)$^+$.

c) bis(6-chloro-2-methoxy-9-acridinyl)-1,3-propane

A mixture of the compound of Example 19 (b) (0.32 g, 1.1 mmol), paraformaldehyde (40 mg), and dimethylamine hydrochloride (0.14 g, 1.7 mmol) in ethanol (4 mL) was heated at 80° for 2.5 h. The suspension was cooled and filtered to give the title compound. MS(ES) m/e 527.3 (M+H)$^+$.

EXAMPLES 20–21

Preparation of bis(2-methoxy-9-acridinyl)-1,4-butane and 1-(6-chloro-2-methoxy-9-acridinyl)-4-(2-methoxy-9-acridinyl)butane a) 2-methyl-4-(6-chloro-2-methoxy-9-acridinyl)-3-butyn-2-ol A mixture of 6,9dichloro-2-methoxyacridine (3.5 g, 12.6 mmol), 2-methyl-3-butyn-2-ol (1.27 g, 15 mmol), dichlorobis(triphenylphosphine)palladium (100 mg), and cuprous iodide (25 mg) in triethylamine (35 mL) and dimethylformamide (20 mL) was heated at 90° for 12 h. The mixture was cooled and diluted with aqueous potassium carbonate to give the title compound. MS(ES) m/e 326.2 (M+H)$^+$.

b) 9-ethynyl-6-chloro-2-methoxyacridine

A solution of the compound of Example 20 (a) (2 g, 6.15 mmol) and sodium hydroxide (0.25 g, 6.25 mmol) in toluene (100 mL) was heated to reflux for 5 h. The mixture was concentrated and residue was taken up in dichloromethane, washed with water, dried, and concentrated in vacuo to give the title compound. MS(ES) m/e 268.1 (M+H)$^+$.

c) bis(2-methoxy-9-acridinyl)-1,4-butadiyne

A mixture of the compound of Example 20 (b) (0.272 g, 1 mmol), dichlorobis(triphenylphosphine)palladium(100 mg), cuprous iodide (25 mg), and iodine (0.128 g, 0.5 mmol) in diethylamine (6 mL) and dimethylformamide (3 mL) was stirred for 2 h and filtered to give the title compound.

d) bis(2-methoxy-9-acridinyl)-1,4-butane and 1-(6chloro-2-methoxy-9-acridinyl)-4-(2-methoxy-9-acridinyl)butane A mixture of the compound of Example 20(c) and 10% palladium-on-carbon (0.12 g) in methanol (25 mL) and ethyl acetate (25 mL) was stirred in an atmosphere of hydrogen. After 18 h, the mixture was filtered and the filtrate was concentrated in vacuo and the residue was purified by HPLC (YMC ODS-AQ, 100×250 mm, 80 mL/min, 30% acetonitrile/water/0.1% trifluoroacetic acid, UV detection at 254 nm) to give the title compounds. MS(ES) m/e 473.3 (M+H)$^+$ and 527.3 (M+H)$^+$, respectively.

EXAMPLE 22

Preparation of N-(9-acridinyl)-N'-(6chloro-2-methoxy-9-acridinyl)-1,2-ethanediamine bis (trifluoroacetate)

A mixture of N-(6chloro-2-methoxy-9-acridinyl)-1,2-ethanediamine (0.4 g, 1.3 mmol) and 9-chloroacridine (0.28 g, 1.3 mmol), was heated at 130° C. for 1 min. The resulting suspension was cooled and filtered. The filtate was purified by HPLC (YMC ODS-AQ, 100×250 mm, 80 mL/min, 20% acetonitrile/water-0.1% trifluoroacetic acid, UV detection at 254 nm) to give the title compound as a yellow solid. MS(ES) m/e 479.3 (M+H)$^+$.

EXAMPLE 23

Preparation of N,N'-bis(6-chloro-2-methoxy-9-acridinyl)-N,N'-bis(acetyl)-1,2-ethanediamine To a suspension of N,N'-bis(6-chloro-2-methoxy-9-acridinyl)-1,2-ethanediamine (0.157 g, 0.3 mmol) in dichloromethane (10 mL) was added triethylamine (4.5 mL, 32 mmol) followed by acetic anhydride (3 mL, 32 mmol). After 18 h, the solution was diluted with dichloromethane (100 mL), washed with water, dried and concentrated in vacuo to give yellow solid, which was purified by flash column chromatography (silica gel, 1% methanol:dichloromethane) to give the title compound as a yellow solid. MS(ES) m/e 627.3 (M+H)$^+$.

Biological Data:

CCR5 Receptor Binding Assay:

CHO cell membranes (0.25×10$^6$ cell equivalents) derived from CHO cells stably transfected with CCR5 were incubated with 0.3 $^{125}$I-RANTES in a 96 well plate for 45 min at room temperature (final reaction volume 200 ul). The reaction was terminated by filtration and the filters (GF/C) were washed twelve times with a solution of phosphate buffered saline containing 0.1% bovine serum albumin and 0.05% NaN$_3$. The radioactivity bound to filters was measured by liquid scintillation spectrometry. Non-specific binding was determined in the presence of unlabelled RANTES (10 or 30 nM) and averages 30–50% of total binding.

CCR5 Receptor Functional Assay:

The cellular functional assay used to assess antagonist activity of compounds was RANTES-induced Ca$^{2+}$ mobilization in RBL 2H3 cells stably expressing the hCCR5 receptor (RBL 2H3 hCCR5). Cells were grown to 80–100% confluency in T-150 flasks and washed with phosphate-buffered saline. Cells were lifted from the flasks by treating with 3 mL of 1 mM EDTA for 3 min at room temperature and diluting to 2×10$^6$ cells/mL with Krebs Ringer Henseleit buffer (KRH; 118 mM NaCl, 4.6 mM KCl, 25 mM NaHCO$_3$, 1 mM KH$_2$PO$_4$ and 11 mM glucose) containing 5 mM HEPES (pH 7.4), 1 mM CaCl$_2$, 1 mM MgCl$_2$ and 0.1% BSA and centrifuged at 200 g for 3 min. Cells were resuspended at 2×10$^6$ cells/mL in the same buffer with 2 $\mu$M Fura-2AM, and incubated for 35 min at 37° C. Cells were centrifuged at 200×g for 3 min and resuspended in the same buffer without Fura-2AM, then incubated for 15 min at 37° C. to complete the hydrolysis of intracellular Fura-2AM, and then centrifuged as before. Cells (10$^6$ cells/mL) were resuspended in cold KRH with 5 mM HEPES (pH 7.4), 1 mM CaCl$_2$, 1 mM MgCl$_2$ and 0.1% gelatin and maintained on ice until assayed. For antagonist studies, aliquots (2 mL) of cells were prewarmed at 37° C. for 5 min in 3 mL plastic cuvettes and fluorescence measured in a fluorometer (Johnson Foundation Biomedical Group, Philadelphia, Pa., USA) with magnetic stirring and temperature maintained at 37° C. Excitation was set at 340 nm and emission set at 510 nm. Various concentrations of antagonists or vehicle were added and fluorescence monitored for ~15 sec to ensure that there was no change in baseline fluorescence, followed by the addition of 33 nM RANTES. Maximal Ca$^{2+}$ attained after 33 nM RANTES stimulation was calculated as described by Grynkiewicz el al., (1985). The percent of maximal RANTES-induced Ca$^{2+}$ was determined for each concentration of antagonist and the IC$_{50}$, defined as the concentration of test compound that inhibits 50% of the maximal 33 nM RANTES response, obtained from the concentration-response curves (5–7 concentrations of antagonists).

The compounds of this invention show CCR5 receptor antagonist activity having IC$_{50}$ values in the range of 0.0001 to 100 $\mu$M. The full structure/activity relationship has not yet been established for the compounds of this invention. However, given the disclosure herein, one of ordinary skill in the art can utilize the present assays in order to determine which compounds of formula (I) are ligands of the CCR5 receptor and which bind thereto with an IC$_{50}$ value in the range of 0.0001 to 100 μm.

All publications, including, but not limited to, patents and patent applications cited in this specification, are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration it is believed that one skilled in the art can, given the preceding description, utilize the present invention to its fullest extent. Therefore any examples are to be construed as merely illustrative and not a limitation on the scope of the present invention in any way. The embodiments of the invention in which an exclusive property or privilege is claimed are defined as follows.

What is claimed is:

1. A method of treating a CCR5-mediated disease state in mammals which comprises administering to a mammal in need of such treatment, an effective amount of a compound of formula (IA) or a pharmaceutically acceptable salt thereof:

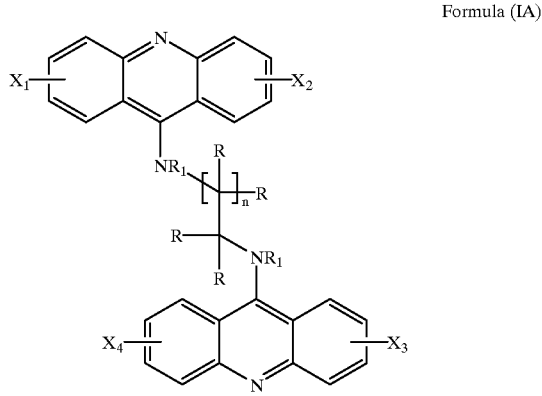

Formula (IA)

wherein:

$X_1$, $X_2$, $X_3$ and $X_4$ are independently one or more of H, OR', or halo;

R' is H or optionally substituted $C_{1-6}$alkyl;

$R_1$ is H, $C_{1-6}$alkyl, or one of $R_1$ is —CO(CF$_3$);

n is 1 or 2; and

R is H or $C_{1-6}$alkyl, provided that when $R_1$ are both H, $X_1$, $X_2$, $X_3$ and $X_4$ are not all hydrogen; and provided that when n is 1, $R_1$ are both H, and $X_2$ and $X_3$ are each hydrogen, $X_1$ and $X_4$ are not each 4-ethyl, 3-methoxy, 4-butoxy; and, provided that when n is 1, and $R_1$ are both H, $X_1$, $X_2$, $X_3$ and $X_4$ are not 2-methoxy-6-chloro; and, provided that when n is 2, and $R_1$ are both H, $X_1$, $X_2$, $X_3$, and $X_4$ are not 2-methoxy-6-chloro or 2-fluoro-6-chloro.

2. A method of treating a CCR5-mediated disease state in mammals which comprises administering to a mammal in need of such treatment, an effective amount of a compound of formula (IA) or a pharmaceutically acceptable salt thereof:

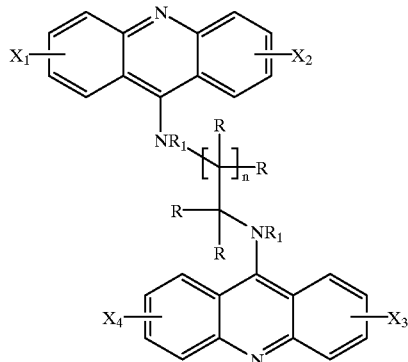

Formula (IA)

wherein:

$X_1$, $X_2$, $X_3$ and $X_4$ are independently one or more of H, OR', or halo;

R' is H or $C_{1-6}$alkyl optionally substituted with N($C_{1-6}$alkyl)$_2$, or CO$_2$C$_{1-6}$alkyl;

$R_1$ is H, CH$_3$, or one of $R_1$ is —CO(CF$_3$);

n is 1 or 2; and

R is H, provided that when $R_1$ are both H, $X_1$, $X_2$, $X_3$ and $X_4$ are not all hydrogen; and, provided that when n is 1, $R_1$ are both H, and $X_2$ and $X_3$ are each hydrogen, $X_1$ and $X_4$ are not each 4-ethyl, 3-methoxy, 4-butoxy; and, provided that when n is 1, and $R_1$ are both H, $X_1$, $X_2$, $X_3$ and $X_4$ are not 2-methoxy-6-chloro; and, provided that when n is 2, and $R_1$ are both H, $X_1$, $X_2$, $X_3$, and $X_4$ are not 2-methoxy-6-chloro or 2-fluoro-6-chloro.

3. A method of treating a CCR5-mediated disease state in mammals which comprises administering to a mammal in need of such treatment, an effective amount of a compound of formula (IA) or a pharmaceutically acceptable salt thereof:

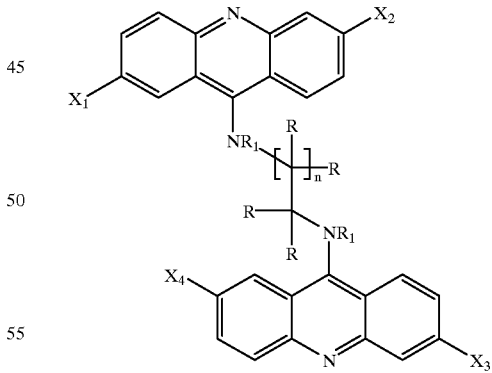

Formula (IA)

wherein:

$X_1$, $X_2$, $X_3$ and $X_4$ are independently one or more of H, OR', or halo;

R' is H or $C_{1-6}$alkyl optionally substituted with N(CH$_3$)$_2$, or CO$_2$C$_{1-6}$alkyl;

$R_1$ is H, CH$_3$, or one of $R_1$ is —CO(CF$_3$);

n is 1 or 2; and

R is H, provided that when $R_1$ are both H, $X_1$, $X_2$, $X_3$ and $X_4$ are not all hydrogen; and, provided that when n is 1, $R_1$ are both H, and $X_2$ and $X_3$ are each hydrogen, $X_1$ and $X_4$ are not each 4-ethyl, 3-methoxy, 4-butoxy; and, provided that when n is 1, and $R_1$ are both H, $X_1$, $X_2$, $X_3$ and $X_4$ are not 2-methoxy-6-chloro; and, provided that when n is 2, and $R_1$ are both H, $X_1$, $X_2$, $X_3$, and $X_4$ are not 2-methoxy-6-chloro or 2-fluoro-6-chloro.

* * * * *